United States Patent
Agrafiotis et al.

(10) Patent No.: US 6,671,627 B2
(45) Date of Patent: Dec. 30, 2003

(54) METHOD AND COMPUTER PROGRAM PRODUCT FOR DESIGNING COMBINATORIAL ARRAYS

(75) Inventors: Dimitris K. Agrafiotis, Downingtown, PA (US); Victor S. Lobanov, North Brunswick, NJ (US); Francis Raymond Salemme, Yardley, PA (US)

(73) Assignee: 3-D Pharmaceuticals, Inc., Exton, PA (US)

( * ) Notice: Subject to any disclaimer, the term of this patent is extended or adjusted under 35 U.S.C. 154(b) by 444 days.

(21) Appl. No.: 09/794,106

(22) Filed: Feb. 28, 2001

(65) Prior Publication Data

US 2001/0029026 A1 Oct. 11, 2001

Related U.S. Application Data

(60) Provisional application No. 60/185,700, filed on Feb. 29, 2000.

(51) Int. Cl.[7] .................. G01N 33/48; G11C 17/00
(52) U.S. Cl. .............................. 702/27; 365/94
(58) Field of Search .................... 702/27; 365/94

(56) References Cited

U.S. PATENT DOCUMENTS

| | | |
|---|---|---|
| 4,773,099 A | 9/1988 | Bokser |
| 4,811,217 A | 3/1989 | Tokizane et al. |
| 4,859,736 A | 8/1989 | Rink |
| 4,908,773 A | 3/1990 | Pantoliano et al. |
| 4,935,875 A | 6/1990 | Shah et al. |
| 4,939,666 A | 7/1990 | Hardman |
| 5,010,175 A | 4/1991 | Rutter et al. |
| 5,025,388 A | 6/1991 | Cramer, III et al. |
| 5,155,801 A | 10/1992 | Lincoln |
| 5,167,009 A | 11/1992 | Skeirik |
| 5,181,259 A | 1/1993 | Rorvig |
| 5,240,680 A | 8/1993 | Zuckermann et al. |
| 5,260,882 A | 11/1993 | Blanco et al. |
| 5,265,030 A | 11/1993 | Skolnick et al. |
| 5,270,170 A | 12/1993 | Schatz et al. |
| 5,288,514 A | 2/1994 | Ellman |
| 5,307,287 A | 4/1994 | Cramer, III et al. |
| 5,323,471 A | 6/1994 | Hayashi |
| 5,331,573 A | 7/1994 | Balaji et al. |
| 5,434,796 A | 7/1995 | Weininger |
| 5,436,850 A | 7/1995 | Eisenberg et al. |
| 5,442,122 A | 8/1995 | Noda et al. |
| 5,463,564 A | 10/1995 | Agrafiotis et al. |
| 5,499,193 A | 3/1996 | Sugawara et al. |
| 5,519,635 A | 5/1996 | Miyake et al. |
| 5,524,065 A | 6/1996 | Yagasaki |
| 5,526,281 A | 6/1996 | Chapman et al. |
| 5,545,568 A | 8/1996 | Ellman |
| 5,549,974 A | 8/1996 | Holmes |
| 5,553,225 A | 9/1996 | Perry |
| 5,565,325 A | 10/1996 | Blake |
| 5,574,656 A | 11/1996 | Agrafiotis et al. |
| 5,585,277 A | 12/1996 | Bowie et al. |
| 5,602,755 A | 2/1997 | Ashe et al. |
| 5,602,938 A | 2/1997 | Akiyama et al. |
| 5,612,895 A | 3/1997 | Balaji et al. |
| 5,634,017 A | 5/1997 | Mohanty et al. |
| 5,635,598 A | 6/1997 | Lebl et al. |
| 5,670,326 A | 9/1997 | Beutel |
| 5,679,582 A | 10/1997 | Bowie et al. |
| 5,684,711 A | 11/1997 | Agrafiotis et al. |
| 5,703,792 A | 12/1997 | Chapman |
| 5,712,171 A | 1/1998 | Zambias et al. |
| 5,712,564 A | 1/1998 | Hayosh |
| 5,736,412 A | 4/1998 | Zambias et al. |
| 5,740,326 A | 4/1998 | Boulet et al. |
| 5,789,160 A | 8/1998 | Eaton et al. |
| 5,807,754 A | 9/1998 | Zambias et al. |
| 5,811,241 A | 9/1998 | Goodfellow et al. |
| 5,832,494 A | 11/1998 | Egger et al. |
| 5,858,660 A | 1/1999 | Eaton et al. |
| 5,861,532 A | 1/1999 | Brown et al. |
| 5,866,334 A | 2/1999 | Beutel |
| 5,901,069 A | 5/1999 | Agrafiotis et al. |
| 5,908,960 A | 6/1999 | Newlander |
| 5,933,819 A | 8/1999 | Skolnick et al. |
| 6,014,661 A | 1/2000 | Ahlberg et al. |
| 6,037,135 A | 3/2000 | Kubo et al. |
| 6,049,797 A | 4/2000 | Guha et al. |
| 6,185,506 B1 | 2/2001 | Cramer et al. |

FOREIGN PATENT DOCUMENTS

| | | |
|---|---|---|
| EP | 0 355 266 B1 | 2/1990 |
| EP | 0 355 628 B1 | 2/1990 |
| EP | 0 770 876 A1 | 5/1997 |
| EP | 0 818 744 A2 | 1/1998 |
| WO | WO 91/19735 | 12/1991 |

(List continued on next page.)

OTHER PUBLICATIONS

Borg, Ingwar and Groenen, Patrick, Modern Multidimensional Scaling Theory and Applications, Springer Series in Statistics, 1997, entire book submitted.

(List continued on next page.)

Primary Examiner—John S. Brusca
(74) Attorney, Agent, or Firm—Pillsbury Winthrop LLP

(57) ABSTRACT

A greedy method for designing combinatorial arrays. An array of reagents are initially selected from a list of candidate reagents in a combinatorial library. The reagents in the array that maximize a design objective are determined in an iterative manner, by examining each variation site in the combinatorial library in a strictly alternating sequence. During each step, each candidate reagent at a given variation site is evaluated by constructing and evaluating the sub-array resulting from the systematic combination of that reagent with the selected reagents at all the other variation sites in the library. The candidate reagents at that variation site are ranked according to the fitness of their respective sub-arrays, and the reagents with the highest fitness are selected. The process is repeated for each variation site in the combinatorial library, until the fitness of the full combinatorial array can no longer be improved.

21 Claims, 20 Drawing Sheets

FOREIGN PATENT DOCUMENTS

| WO | WO 92/00091 | 1/1992 |
| --- | --- | --- |
| WO | WO 93/20242 | 10/1993 |
| WO | WO 94/28504 | 12/1994 |
| WO | WO 95/01606 | 1/1995 |
| WO | WO 97/09342 | 3/1997 |
| WO | WO 97/20952 | 6/1997 |
| WO | WO 97/27559 | 7/1997 |
| WO | WO 98/20437 | 5/1998 |
| WO | WO 98/20459 | 5/1998 |

OTHER PUBLICATIONS

Agrafiotis, D.K. et al., "Advances in diversity and combinatorial series design," *Molecular Diversity*, Kluwer Academic Publishers, vol. 4, 1999, pp. 1–22.

Agrafiotis, D.K. and Lobanov, V.S., "An Efficient Implementation of Distance–Based Diversity Measures Based on k–d Trees," *Journal of Chemical Information and Computer Science*, American Chemical Society, vol. 39, No. 1, Jan./Feb. 1999, pp. 51–58.

Agrafiotis, D.K. and Lobanov, V.S., "Bridging The Gap Between Diversity And QSAR," Abstracts of Papers Part 1:215th ACS National Meeting, American Chemical Society, Mar. 29–Apr. 2, 1998, p. 181–COMP.

Agrafiotis, D.K. and Jaegar, E.P., "Directed Diversity®: An Operating System For Combinatorial Chemistry," Abstracts of Paper Part 1: 211th ACS National Meeting, American Chemical Society, Mar. 24–28, 1996, p. 46–COMP.

Agrafiotis, D.K., "Diversity of Chemical Libraries," *Encyclopedia of Computational Chemistry*, John Wiley & Sons Ltd, vol. 1:A–D, 1998, pp. 742–761.

Agrafiotis, D.K., "On the Use of Information Theory for Assessing Molecular Diversity," *Journal of Chemical Information and Computer Science*, American Chemical Society, vol. 37, No. 3, May/Jun. 1997, pp. 576–580.

Agrafiotis, D.K. et al., "Parallel QSAR," Abstracts of Papers 1: 217th ACS National Meeting, Mar. 21–25, 1999, p. 50–COMP.

Agrafiotis, D.K. et al., "PRODEN: A New Program for Calculating Integrated Projected Populations," *Journal of Computational Chemistry*, John Wiley & Sons, Inc., vol. 11, No. 9, Oct. 1990, pp. 1101–1110.

Agrafiotis, D.K. and Jaeger, E.P., "Stochastic Algorithms for Exploring Molecular Diversity," Abstracts of Papers Part 1: 213th ACS National Meeting, American Chemical Society, Apr. 13–17, 1997, p. 16–CINF.

Agrafiotis, D., "Theoretical Aspects of the Complex: Arts and New Technologies," *Applications and Impacts Information Processing '94*, North–Holland, vol. II, 1994, pp. 714–719.

Biswas, G. et al., "Evaluation of Projection Algorithms," *IEEE Transactions On Pattern Analysis And Machine Intelligence*, IEEE Computer Society, vol. PAMI–3, No. 6, Nov. 1981, pp. 701–708.

Bonchev, D. and Trinajstić, N., "Information theory, distance matrix, and molecular branching," *The Journal of Chemical Physics*, American Institute of Physics, vol. 67, No. 10, Nov. 15, 1977, pp. 4517, 4520–4533.

Chang, C.L. and Lee, R.C.T., "A Heuristic Relaxation Method of Nonlinear Mapping in Cluster Analysis," *IEEE Transactions of Systems, Man, and Cybernetics*, IEEE Systems, Man, and Cybernetics Society, vol. SMC–3, Mar. 1973, pp. 197–200.

Cramer, R.D. et al., "Virtual Compound Libraries: A New Approach to Decision Making in Molecular Discovery Research," *J. Chem. Inf. Comput. Sci.*, American Chemical Society, vol. 38, No. 6, Nov./Dec. 1998, pp. 1010–1023.

DeMers, D. and Cottrell, G., "Non–Linear Dimensionality Reduction," *Advances in Neural Information Processing Systems*, vol. 5, 1993, pp. 580–587.

Frey, P.W. and Slate, D.J., "Letter Recognition Using Holland–Style Adaptive Classifiers," *Machine Learning*, Kluwer Academic Publishers, vol. 6, 1991, pp. 161–182.

Friedman, J.H., "Exploratory Projection Pursuit," *Journal of the American Statistical Association*, American Statistical Association, vol. 82, No. 397, Mar. 1987, pp. 249–266.

Friedman, J.H. and Turkey, J.W., "A Projection Pursuit Algorithm for Exploratory Data Analysis," *IEEE Transactions on Computers*, IEEE Computer Society, vol. C–23, No. 9, Sep. 1974, pp. 881–889.

Garrido, L. et al., "Use of Multilayer Feedforward Neural Nets As A Display Method for Multidimensional Distributions," *International Journal of Neural Systems*, World Scientific Publishing Co. Pte. Ltd., vol. 6, No. 3, Sep. 1995, pp. 273–282.

Ghose, A.K. et al., "Prediction of Hydrophobic (Lipophilic) Properties of Small Organic Molecules Using Fragmental Methods: An Analysis of ALOGP and CLOGP Methods," *Journal of Physical Chemistry*, American Chemical Society, vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances*, VCH Publishers, Inc., 1991, pp. 367–422.

Hecht–Nielsen, R., "Replicator Neural Networks for Universal Optimal Source Coding," *Science*, American Association for the Advancement of Science, vol. 269, Sep. 29, 1995, pp. 1860–1863.

Hotelling, H., "Analysis of a Complex of Statistical Variables into Principal Components," *The Journal of Educational Psychology*, Warwick and York, Inc., vol. XXIV, No. 6, Sep. 1933, pp. 417–441.

Hotelling, H., "Analysis of a Complex of Statistical Variables into Principal Components," *The Journal of Educational Psychology*, Warwick and York, Inc., vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers*, The Institute of Electrical and Electronics Engineers, Mar. 1977, pp. 288–292.

Lipinski, C.A. et al., "Experimental and computational approaches to estimate solubility and permeability in drug discovery and development settings," *Advanced Drug Delivery Reviews*, Elsevier Science B.V., vol. 23, 1997, pp. 3–25.

Lobanov, V.S. and Agrafiotis, D.K., "Intelligent Database Mining Techniques," *Abstracts of Papers Part 1:215th ACS National Meeting*, Mar. 29–Apr. 2, 1998, p. 19–COMP.

Mao, J. and Jain, A.K., "Artificial Neural Networks for Feature Extraction and Multivariate Data Projection," *IEEE transactions on Neural Networks*, IEEE Neural Networks, vol. 6, No. 2, Mar. 1995, pp. 296–317.

Oja, E., "Principal Components, Minor Components, and Linear Neural Networks," *Neural Networks*, Pergamon Press Ltd., vol. 5, 1992, pp. 927–935.

Patterson, D.E. et al., "Neighborhood Behavior: A Useful Concept for Validation of 'Molecular Diversity' Descriiptors," *Journal of Medicinal Chemistry*, American Chemical Society, vol. 39, No. 16, 1996, pp. 3049–3059.

Pykett, C.E., "Improving the Efficiency of Sammon's Nonlinear Mapping by Using Clustering Archetypes," *Electronics Letters*, The Institution of Electrical Engineers, vol. 14, No. 25, Dec. 7, 1978, pp. 799–800.

Rubner, J. and Tavan, P., "A Self–Organizing Network for Principal–Component Analysis," *Europhysics Letters*, European Physical Society, vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Chemie*, VCH, vol. 34, No. 23/24, Jan. 5, 1996, pp. 2674–2677.

Thompson, L.A. and Ellman, J.A., "Synthesis and Applications of Small Molecule Libraries," *Chemical Reviews*, American Chemical Society, vol. 96, No. 1, Jan./Feb. 1996, pp. 555–585, 588–600.

Barnard, John M. and Downs, Geoff M., "Computer representation and manipulation of combinatorial libraries," *Perspectives in Drug Discovery and Design*, Kluwer Academic Publishers, 1997, pp. 13–30.

Brint, Andrew T. and Willett, Peter, "Upperbound procedures for the identification of similar three–dimensional chemical structures," *Journal of Computer–Aided Molecular Design*, ESCOM Science Publishers B.V., vol. 2, No. 4, Jan. 1989, pp. 311–320.

Brown, Robert D. and Martin, Yvonne C., "Designing Combinatorial Library Mixtures Using a Genetic Algorithm," *Journal of Medicinal Chemistry*, American Chemical Society, vol. 40, No. 15, 1997, pp. 2304–2313.

Gillet, Valerie J. et al., "The Effectiveness of Reactant Pools for Generating Structurally–Diverse Combinatorial Libraries," *Journal of Chemical Computer Sciences*, American Chemical Society, vol. 37, No. 4, 1997, pp. 731–740.

Gillet, Valerie J. et al., "Selecting Combinatorial Libraries to Optimize Diversity and Physical Properties," *Journal of Chemical Information and Computer Sciences*, American Chemical Society, vol. 39, No. 1, 1999, pp. 169–177.

Kearsley, Simon K. et al., "Chemical Similarity Using Physiochemical Property Descriptors," *Journal of Chemical Information and Computer Sciences*, American Chemical Society, vol. 36, No. 1, 1996, pp. 118–127.

Leland, Burton A. et al., "Managing the Combinatorial Explosion," *Journal of Chemical Information and Computer Sciences*, American Chemical Society, vol. 37, No. 1, 1997, pp. 62–70.

Lewis, Richard A. et al., "Similarity Measures for Rational Set Selection and Analysis of Combinatorial Libraries: The Diverse Property–Derived (DPD) Approach," *Journal of Chemical Information Computer Science*, American Chemical Society, vol. 37, No. 3, 1997, pp. 599–614.

Martin, Eric J. and Critchlow, Roger E., "Beyond Mere Diversity: Tailoring Combinatorial Libraries for Drug Discovery," *Journal of Combinatorial Chemistry*, American Chemical Society, vol. 1, No. 1, 1999, pp. 32–45.

Sheridan, Robert P. et al., "Chemical Similarity Using Geometric Atom Pair Descriptors," *Journal of Chemical Information and Computer Sciences*, American Chemical Society, vol. 36, No. 1, 1996, pp. 128–136.

Willett, Peter et al., "Chemical Similarity Searching," *Journal of Chemical Information and Computer Sciences*, American Chemical Society, vol. 38, No. 6, 1998, pp. 983–996.

Agrafiotis, Dimitris K. and Lobanov, Victor S., "Ultrafast Algorithm for Designing Focused Combinatorial Arrays," *Journal of Chemical Information and Computer Sciences*, American Chemical Society, 2000, vol. 40, No. 4, pp. 1030–1038.

Ajay et al., "Can We Learn To Distinguish between 'Drug–Like' and 'Nondrug–like' Molecules?" *J. Med. Chem.*, 1998, American Chemical Society, vol. 41, No. 18, pp. 3314–3324.

Brown, Robert D. and Martin, Yvonne C., "The Information Content of 2D and 3D Structural Descriptors Relevant to Ligand–Receptor Binding," *Journal of Chemical Information and Computer Sciences*, American Chemical Society, 1997, vol. 37, No. 1, pp. 1–9.

Brown, Robert D. and Martin, Yvonne C., "Use of Strucuture–Activity Data To Compare Structure–Based Clustering Methods and Descriptors for Use in Compound Selection," *Journal of Chemical Information and Computer Sciences*, American Chemical Society, 1996, vol. 36, No. 3, pp. 572–584.

Cummins, David J. et al., "Molecular Diversity in Chemical Databases: Comparison of Medicinal Chemistry Knowledge Bases and Databases of Commercially Available Compounds," *Journal of Chemical Information and Computer Sciences*, American Chemical Society, 1996, vol. 36, No. 4, pp. 750–763.

Domine, D. et al., "Non–Linear Mapping for Structure–Activity and Structure–Property Modelling," *Journal of Chemometrics*, John Wiley & Sons, Ltd., vol. 7, No. 4, Jul.–Aug. 1993, pp. 227–242.

Hosenpud, J. et al., "The Effect of Transplant Center Volume on Cardiac Transplant Outcome: A Report of the United Network for Organ Sharing Scientific Registry," *Journal of the American Medical Association*, American Medical Association, vol. 271, No. 23, Jun. 15, 1994, pp. 1844–1849.

Downs, Geoff M. and Barnard, John M., "Techniques for Generating Descriptive Fingerprints in Combinatorial Libraries," *Journal of Chemical Information and Computer Sciences*, American Chemical Society, 1997, vol. 37, No. 1, pp. 59–61.

Gillet, Valerie J., "Background Theory of Molecular Diversity," *Molecular Diversity in Drug Design*, Kluwer Academic Publishers, 1999, pp. 43–65.

Good, Andrew C. and Lewis, Richard A., "New Methodology for Profiling Combinatorial Libraries and Screening Sets: Cleaning Up the Desing Process with HARPick," *Journal of Medicinal Chemistry*, American Chemical Society, 1997, vol. 40, No. 24, pp. 3926–3936.

Pal, N.R. and Eluri, V.K., "Two Efficient Connectionist Schemes for Structure Preserving Dimensionally Reduction," *IEEE Transactions on Neural Networks*, IEEE, vol. 9, No. 6, Nov. 1998, pp. 1142–1154.

Jamois, Eric A. et al., "Evaluation of Reagent–Based on Product–Based Strategies in the Design of Combinatorial Library Subsets," *Journal of Chemical Information and Computer Sciences*, American Chemical Society, 2000, vol. 40, No. 1, pp. 63–70.

Leach, Andrew R. et al., "Implementation of a System for Reagent Selection and Library Enumeration, Profiling, and Design," *Journal of Chemical Information and Computer Sciences*, American Chemical Society, 1999, vol. 39, No. 6, pp. 1161–1172.

Kim, H. et al., "Self–Organized Distibuted Networks for Learning Highly Nonlinear Mapping," *Intelligent Engineering Systems Through Artificial Neural Networks*, American Society of Mechanical Engineers, vol. 4, Nov. 13–16, 1994, pp. 109–114.

Leland, Burton A. et al., "Managing the Combinatorial Explosion," *Journal of Chemical Information and Computer Sciences*, American Chemical Society, 1997, vol. 37, No. 1, pp. 62–70.

Lobanov, Victor S. and Agrafiotis, Dimitris K., "Stochastic Similarity Selections from Large Combinatorial Libraries," *Journal of Chemical Information and Computer Sciences*, American Chemical Society, Mar./Apr. 2000, vol. 40, No. 2, pp. 460–470.

Matter, Hans and Pötter, Thorsten, "Comparing 3D Pharmacophore Triplets and 2D Fingerprints for Selecting Diverse Compound Subsets," *Journal of Chemical Information and Computer Sciences*, American Chemical Society, 1999, vol. 39, No. 6, pp. 1211–1225.

Matter, Hans, "Selecting Optimally Diverse Compounds from Structure Databases: A Validation Study of Two–Dimensional and Three–Dimensional Molecular Descriptors," *Journal of Medicinal Chemistry*, American Chemical Society, 1997, vol. 40, No. 8, pp. 1219–1229.

Sadowski, Jens and Kubinyi, Hugo, "A Scoring Scheme for Discriminating between Drugs and Nondrug," *Journal of Medicinal Chemistry*, American Chemical Society, 1998, vol. 41, No. 18, pp. 3325–3329.

Schnur, Dora, "Design and Diversity Analysis of Large Combinatorial Libraries Using Cell–Based Methods," *Journal of Chemical Information and Computer Science*, American Chemical Society, 1999, vol. 39, No. 1, pp. 36–45.

Schuffenhauer, Ansgar et al., "Similarity Searching in Files of Three–Dimensional Chemical Structures: Analysis of the BIOSTER Database Using Two–Dimensional Fingerprinting and Molecular Field Descriptors," *Journal of Chemical Information and Computer Science*, American Chemical Society, 2000, vol. 40, No. 2, pp. 295–307.

Turner, David B. et al., "Rapid Quantification of Molecular Diversity for Selective Database Acquisition," *Journal of Chemical Information and Computer Science*, American Chemical Society, 1997, vol. 37, No. 1, pp. 18–22.

Wang, Jing and Ramnarayan, Kal, "Toward Designing Drug–Like Libraries: A Novel Computational Approach for Prediction of Drug Feasibility of Compounds," *Journal of Combinatorial Chemistry*, American Chemical Society, Nov./Dec. 1999, vol. 1, No. 6, pp. 524–533.

Gasteiger, J. et al., "Assessment of the Diversity of Combinatorial Libraries by an Encoding of Molecular Surface Properties," *Abstracts of Papers Part 1: 211th ACS National Meeting*, Mar. 24–28, 1996, P. 70–CINF.

Hassan, Moises et al., "Optimization and visualization of molecular diversity of combinatorial libraries," *Molecular Diversity*, ESCOM Science Publishers B.V., 1996, vol. 2, pp. 64–74.

Bellman, R.E., Adaptive Control Processes: A Guided Tour, Princeton Univ. Press, Princeton, NJ (1961), entire book submitted.

Bezdek, J.C., Pattern Recognition with Fuzzy Objective Function Algorithms, Plenum Press, New York, NY (1981), entire book submitted.

Johnson, M.A., and Maggiora, G.M., *Concepts and Applications of Molecular Similarity*, John Wiley and Sons, New York, NY (1990), entire book submitted.

Kohonen, T., *Self–Organizing Maps*, Springer–Verlag, Heidelberg, Germany (1995), entire book submitted.

Oja, E., Subspace Methods of Pattern Recognition, Research Studies Press Ltd., Letchworth, England (1983), entire book submitted.

Agrafiotis, D.K., "A New Method For Analyzing Protein Sequence Relationships Based ON Sammon Maps," *Protein Science*, Cambridge University Press, vol. 6, No. 2, Feb. 1997, pp. 287–293.

Amzel, L.M., "Structure–based drug design," *Current Opinion in Biotechnology*, vol. 9, No. 4, Aug. 1998, pp. 366–369.

Blaney, J.M. and Martin, E.J., "Computational approaches for combinatorial library design and molecular diversity analysis," *Current Opinion in Chemical Biology*, Current Biology Ltd., vol. 1, No. 1, Jun. 1997, pp. 54–59.

Cafisch, A. and Karplus, M., "Computational combinatorial chemistry for de novo ligand design: Review and assessment," *Perspectives in Drug Discovery and Design*, ESCOM Science Publishers B.V., vol. 3, 1995, pp. 51–84.

Eichler, U. et al., "Addressing the problem of molecular diversity," *Drugs of the Future*, Prous Science, vol. 24, No. 2, 1999, pp. 177–190.

Felder, E.R. and Poppinger, D., "Combinatorial Compound Libraries for Enhanced Drug Discovery Approaches," *Advances in Drug Research*, Academic Press, vol. 30, 1997, pp. 112–199.

Geysen, H.M. and Mason, T.J., "Screening Chemically Synthesized Peptide Libraries for Biologically–Relevant Molecules," *Bioorganic & Medicinal Chemistry Letters*, Pergamon Press Ltd., vol. 3, No. 3, 1993, pp. 397–404.

Gobbi, A. et al., "New Leads By Selective Screening of Compounds From Large Databases," *Abstracts of Papers Part 1: 213th ACS National Meeting*, American Chemical Society, Apr. 13–17, 1997, p. 67–CINF.

Houghton, R.A. et al., "The Use of Synthetic Peptide Combinatorial Libraries for the Identification of Bioactive Peptides," *Peptide Research*, vol. 5, No. 6, 1992, pp. 351–358.

Klopman, G., "Artificial Intelligence Approach to Structure–Activity Studies. Computer Automated Structure Evaluation of Biological Activity of Organic Molecules," *Journal of the American Chemical Society*, American Chemical Society, vol. 106, No. 24, 1984, pp. 7315–7321.

Lajiness, M.S. et al., "Implementing Drug Screening Programs Using Molecular Similarity Methods," *QSAR: Quantitative Structure–Activity Relationships in Drug Design*, Alan R. Liss, Inc., 1989, pp. 173–176.

Loew, G.H. et al., "Strategies for Indirect Computer–Aided Drug Design," *Pharmaceutical Research*, Plenum Publishing Corporation, vol. 10, No. 4, 1993, pp. 475–486.

Lynch, M.F. et al., "Generic Structure Storage and Retrieval," *Journal of Chemical Information and Computer Sciences*, American Chemical Society, vol. 25, No. 3, Aug. 1985, pp. 264–270.

Myers, P.L. et al., "Rapid, Reliable Drug Discovery, " Today's Chemist At Work, American Chemical Society, vol. 6, No. 7, Jul./Aug. 1997, pp. 46–48, 51 & 53.

Pabo, C.O. and Suchanek, E.G., "Computer–Aided Model–Building Strategies for Protein Design," *Biochemistry*, American Chemical Society, vol. 25, No. 20, 1986, pp. 5987–5991.

Saudek, V. et al., "Solution Conformation of Endothelin–1 by H NMR, CD, and Molecular Modeling," *International Journal of Peptide Research*, Munksgaard International Publishers Ltd., vol. 37, No. 3, 1991, pp. 174–179.

Singh, J. et al., "Application of Genetic Algorithms to Combinatorial Synthesis: A Computational Approach to Lead Identification and Lead Optimization," *J. Am. Chem. Soc.*, American Chemical Society, vol. 118, No. 7, Feb. 7, 1996, pp. 1669–1676.

Van Drie, J.H. and Lajiness, M.S., "Approaches to virtual library design," *Drug Discovery today*, Elsevier Science Ltd., vol. 3, No. 6, Jun. 1998, pp. 274–283.

Walters, W.P. et al., "Virtual screening—an overview," *Drug Discovery today*, Elsevier Science Ltd., vol. 3, No. 4, Apr. 1998, pp. 160–178.

Weber, L., "Evolutionary combinatorial chemistry: application of genetic algorithms," *Drug Discovery today*, Elsevier Science Ltd., vol. 3, No. 8, Aug. 1998, pp. 379–385.

Weber, L. et al., "Optimization of the Biological Activity in Combinatorial Compound Libraries by a Genetic Algorithm," *Angewandte Chemie International Edition in English*, VCH, vol. 34, No. 20, Nov. 3, 1995, pp. 2280–2282.

Graybill, T.L. et al., "Enhancing the Drug Discovery Process by Integration of High–Throughput Chemistry and Structure–Based Drug Design," from Molecular Diversity and Combinatorial Chemistry: Libraries and Drug Discovery, Chaiken and Janda (eds.), American Chemical Society, 1996, pp. 16–27.

Saund, E., "Dimensionally–Reduction Using Connectionist Networks," *IEEE Transactions on Pattern Analysis and Machine Intelligence*, IEEE, vol. 11, No. 3, Mar. 1989, pp. 304–314.

"3DP gains drug research patent", *Chemistry in Britain*, The Royal Society of Chemistry, vol. 32, No. 1, Jan. 1996, p. 22.

"Accelerate the Discovery Cycle with Chem–X!", Source and date of publication unclear, 2 pages.

Agrafiotis, D. K., "Stochastic Algorithms for Maximizing Molecular Diversity", *Journal of Chemical Information and Computer Sciences*, American Chemical Society, vol. 37, No. 5, 1997, pp. 841–851.

Alsberg, B.K. et al., "Classification of pyrolysis mass spectra by fuzzy multivariate rule induction–comparison with regression, K–nearest neighbour, neural and decision–tree methods", *Analytica Chimica Acta*, Elsevier Science B.V., vol. 348, No. 1–3, Aug. 20, 1997, pp. 389–407.

Andrea, T.A. and Kalayeh, H., "Applications of Neural Networks in Quantitative Structure–Activity Relationships of Dihydrofolate Reductase Inhibitors", *Journal of Medicinal Chemistry*, American Chemical Society, vol. 34, No. 9, 1991, pp. 2824–2836.

Aoyama, T. et al., "Neural Networks Applied to Quantitative Structure–Activity Relationship Analysis", *Journal of Medicinal Chemistry*, American Chemical Society, vol. 33, No. 9, 1990, pp. 2583–2590.

Aoyama, T. and Ichikawa, H., "Obtaining the Correlation Indices between Drug Activity and Structural Parameters Using a Neural Network", *Chemical & Pharmaceutical Bulletin*, Pharmaceutical Society of Japan, vol. 39, No. 2, Feb. 1991, pp. 372–378.

Baum, R.M., "Combinatorial Approaches Provide Fresh Leads for Medicinal Chemistry", *Chemical & Engineering News*, American Chemical Society, Feb. 7, 1994, pp. 20–26.

Bentley, J. L., "Multidimensional Binary Search Trees Used for Associative Searching", *Communications of the ACM*, Association for Computing Machinery, Inc., vol. 18, No. 9, Sep. 1975, pp. 509–517.

Bottou, L. and Vapnik, V. "Local Learning Algorithms", *Neural Computation*, Massachusetts Institute of Technology, vol. 4, No. 6, Nov. 1992, pp. 888–900.

Boulu, L.G. and Crippen, G.M., "Voronol Binding Site Models: Calculation of Binding Modes and Influence of Drug Binding Data Accuracy", *Journal of Computational Chemistry*, John Wiley & Sons, Inc., vol. 10, No. 5, Jul./Aug. 1989, pp. 673–682.

Boulu, L.G. et al., "Voronoi Binding Site Model of a Polycyclic Aromatic Hydrocarbon Binding Protein", *Journal of Medicinal Chemistry*, American Chemical Society, vol. 33, No. 2, 1990, pp. 771–775.

Brown, R. D. and Martin, Y.C., "Use of Structure–Activity Data To Compare Structure–Based Clustering Methods and Descriptors for Use in Compound Selection", *Journal of Chemical Information and Computer Sciences*, vol. 36, No. 3, 1996, pp. 572–584.

Cacoullos, T., "Estimation of a Multivariate Density", *Annals of The Institute of Statistical Mathematics*, The Institute of Statistical Mathematics, vol. 18, No. 2, 1996, pp. 179–189.

Clark, R.D., "OptiSim: An Extended Dissimilarity Selection Method for Finding Diverse Representative Subsets", *Journal of Chemical information and Computer Sciences*, American Chemical Society, vol. 37, No. 6, 1997, pp. 1181–1188.

Clark, D. E., and Westhead, D.R., "Evolutionary algorithms in computer–aided molecular design", *Journal of Computer–Aided Molecular Design*, ESCOM Science Publishers B.V., vol. 10, No. 4, Aug. 1996, pp. 337–358.

Cramer, III, R. D. et al., "Comparative Molecular Field Analysis (CoMFA). 1. Effect of Shape on Binding of Steroids to Carrier Proteins", *Journal of The American Chemical Society*, American Chemical Society, vol. 110, No. 18, Aug. 31, 1988, pp. 5959–5967.

Cramer, III, R. D. et al., "Substructural Analysis. A Novel Approach to the Problem of Drug Design", *Journal of Medicinal Chemistry*, vol. 17, No. 5, May 1974, pp. 533–535.

Crippen, G. M., "Voronoi Binding Site Models", *Journal of Computational Chemistry*, John Wiley & Sons, Inc., vol. 8, No. 7, Oct./Nov. 1987, pp. 943–955.

Friedman, J. H. et al., "An Algorithm for Finding Best Matches in Logarithmic Expected Time", *ACM Transactions on Mathematical Software*, Association for Computing Machinery, vol. 3, No. 3, Sep. 1977, pp. 209–226.

Friedman, J.H., "Fitting Functions To Noisy Data In High Dimensions", Department of Statistics–Stanford University Technical Report No. 101, (Aug., 1988), pp. 1–36.

Gallop, M. A. et al., "Applications of Combinatorial Technologies to Drug Discovery. 1. Background and Peptide Combinatorial Libraries", *Journal of Medicinal Chemistry*, American Chemical Society, vol. 37, No. 9, Apr. 29, 1994, pp. 1233–1251.

Ghose, A. K. and Crippen, G.M., "Use of Physiocochemical Parameters in Distance Geometry and Related Three–Dimensional Quantitative Structure–Activity Relationships: A Demonstration Using *Escherichia coli* Dihydrofolate Reductase Inhibitors", *Journal of Medicinal Chemistry*, American Chemical Society, vol. 28, No. 3, 1985, pp. 333–346.

Good, A. C. et al., "Structure–Activity Relationships from Molecular Similarity Matrices", *Journal of Medicinal Chemistry*, American Chemical Society, vol. 36, No. 4, Feb. 19, 1993, pp. 433–438.

Gordon, E. M. et al., "Applications of Combinatorial Technologies to Drug Discovery. 2. Combinatorial Organic Synthesis, Library Screening Strategies, and Future Directions", *Journal of Medicinal Chemistry*, American Chemical Society, vol. 37, No. 10, May 13, 1994, pp. 1385–1401.

Hartigan, J.A., "Representation of Similarity Matrices By Trees", *Journal of the American Statistical Association*, vol. 62, No. 320, Dec., 1967, pp. 1140–1158.

Hopfinger, A. J., "A QSAR Investigation of Dihydrofolate Reductase Inhibition by Baker Triazines Based upon Molecular Shape Analysis", *Journal of the American Chemical Society*, American Chemical Society, vol. 102, No. 24, Nov. 19, 1980, pp. 7196–7206.

Jackson, R. C., "Update on computer–aided drug design", *Current Opinion in Biotechnology*, Current Biology Ltd., vol. 6, No. 6, Dec. 1995, pp. 646–651.

Kim, K. H., "Comparative molecular field analysis (CoMFA)", *Molecular Similarity in Drug Design*, ed. P. M. Dean, Blackie Academic & Professional, 1995, Ch. 12, pp. 291–331.

Kohonen, T., "Self–Organized Formation of Topologically Correct Feature Maps", *Biological Cybernetics*, Springer–Verlag, vol. 43, No. 1, 1982, pp. 59–69.

Koile, K. and Shapiro, R., "Building A Collaborative Drug Design System", *Proceedings of the 25th Hawaii International Conference on System Sciences*, IEEE, 1992, pp. 706–716.

Kowalski, B. R. and Bender, C. F., "Pattern Recognition. II. Linear and Nonlinear Methods for Displaying Chemical Data", *Journal of the American Chemical Society*, American Chemical Society, vol. 95, No. 3, Feb. 7, 1973, pp. 686–693.

Kruskal, J.B., "Nonmetric Multidimensional Scaling: A Numerical Method", *Psychometrika*, vol. 29, No. 2, Jun., 1964, pp. 115–129.

Lengauer, T. and Rarey, M., "Computational methods for biomolecular docking", *Current Opinion in Structural Biology*, Current Biology Ltd, vol. 6, No. 3, Jun., 1996, pp. 402–406.

Luke, B. T., "Evolutionary Programming Applied to the Development of Quantitative Structure–Activity Relationships and Quantitative Structure–Property Relationships", *Journal of Chemical Information and Computer Sciences*, American Chemical Society, vol. 34, No. 6, Nov./Dec. 1994, pp. 1279–1287.

Martin, E. J. et al., "Does Combinatorial Chemistry Obviate Computer–Aided Drug Design?", *Reviews in Computational Chemistry*, VCH Publishers, Inc., vol. 10, 1997, pp. 75–99.

Martin, E. J. et al., "Measuring Diversity: Experimental Design of Combinatorial Libraries for Drug Discovery", *Journal of Medicinal Chemistry*, American Chemical Society, vol. 38, No. 9, Apr. 28, 1995, pp. 1431–1436.

McMartin, C. and Bohacek, R.S., "QXP: Powerful, rapid computer algorithms for structure–based drug design", *Journal of Computer–Aided Molecular Design*, Kluwer Academic Publishers, vol. 11, No. 4, Jul. 1997, pp. 333–344.

Mezey, P. G. and Walker, P.D., "Fuzzy molecular fragments in drug research", *Drug Discovery today*, vol. 2, No. 4, Apr. 1997, pp. 132–137.

Müller, K., "On the paradigm shift from rational to random design", *Journal of Molecular Structure* (Theochem), Elsevier Science B.V., vol. 398–399, Special Issue, 1997, pp. 467–471.

Omohundro, S. M., "Bumptrees for Efficient Function, Constraint, and Classification Learning", *Advances in Neural Information Processing Systems 3*, Morgan Kaufmann, 1991, 7 pages, unknown.

Parrill, A.L., "Evolutionary and genetic methods in drug design", *Drug Discovery today*, Elsevier Science Ltd., vol. 1, No. 12, Dec. 1996, pp. 514–521.

Polanski, J., "A neural network for the simulation of biological systems", *Journal of Molecular Structure (Theochem)*, Elsevier Science Ltd., vol. 398–399, Special Issue, 1997, pp. 565–571.

Ramos–Nino, M. E. et al., "A comparison of quantitative structure–activity relationships for the effect of benzoic and cinnamic acids on *Listeria monocytogenes* using multiple linear regression, artificial neural network and fuzzy systems", *Journal of Applied Microbiology*, Society for Applied Bacteriology, vol. 82, No. 2, Feb. 1997, pp. 168–176.

Rogers, D. and Hopfinger, A. J., "Application of Genetic Function Approximation to Quantitative Structure–Activity Relationships and Quantitative Structure–Property Relationships", *Journal of Chemical Information and Computer Sciences*, American Chemical Society, vol. 34, No. 4, Jul./Aug. 1994, pp. 854–866.

Sammon, Jr., J. W., "A Nonlinear Mapping for Data Structure Analysis", *IEEE Transactions on Computers*, IEEE, vol. C–18, No. 5, May 1969, pp. 401–409.

Simon, Z. et al., "Mapping of Dihydrofolate–reductase Receptor Site by Correlation with Minimal Topological (Steric) Differences", *Journal of Theoretical Biology*, Academic Press, Inc., vol. 66, No. 3, Jun. 7, 1997, pp. 485–495.

Smellie, A. S. et al., "Fast Drug–Receptor Mapping by Site–Directed Distances: A Novel Method of Predicting New Pharmacological Leads", *Journal of Chemical Information and Computer Sciences*, American Chemical Society, vol. 31, No. 3, Aug. 1991, pp. 386–392.

Specht, D. F., "A General Regression Neural Network", *IEEE Transactions on Neural Networks*, IEEE, vol. 2, No. 6, Nov. 1991, pp. 568–576.

Svozil, D. et al., "Neural Network Prediction of the Solvatochromic Polarity/Polarizability Parameter $\pi^{H}_{2}$", *Journal of Chemical Information and Computer Sciences*, American Chemical Society, vol. 37, No. 2, 1997, pp. 338–342.

Todorov, N. P. and Dean, P. M., "Evaluation of a method for controlling molecular scaffold diversity in de novo ligand design", *Journal of Computer–Aided Molecular Design*, ESCOM Science Publishers B.V., vol. 11, 1997, pp. 175–192.

Torgerson, W.S., "Multidimensional Scaling: I. Theory and Method", *Psychometrika*, The Psychometric Society, vol. 17, No. 4, Dec. 1952, pp. 401–419.

Vapnik, V., "Principles of Risk Minimization for Learning Theory", *Advances in Neural Information Processing Systems 4*, Morgan Kaufmann Publishers, Inc., 1992, pp. 831–838.

Vapnik, V. and Bottou, L., "Local Algorithms for Pattern Recognition and Dependencies Estimation", *Neural Computation*, Massachusetts Institute of Technology, vol. 5, No. 6, Nov. 1993, pp. 893–909.

Viswandhan, V. N. et al., "Mapping the binding site of the nucleoside transporter protein: a 3D–QSAR study", *Biochimica et Biophysica Acta*, Elsevier Science Publishers B.V., vol. 1039, No. 3, 1990, pp. 356–366.

Westhead, D. R. et al., "A comparison of heuristic search algorithms for molecular docking", *Journal of Computer–Aided Molecular Design*, Kluwer Academic Publishers, vol. 11, 1997, pp. 209–228.

Willett, P., "Genetic algorithms in molecular recognition and design", *Trends in Biotechnology*, Elsevier Science Publishers B.V., vol. 13, No. 12, Dec. 1995, pp. 516–521.

Willett, P. and Winterman, V., "A Comparison of Some Measures for the Determination of Inter–Molecular Structural Similarity Measures of Inter–Molecular Structural Similarity", *Quantitative Structure–Activity Relationships*, VCH, vol. 5, No. 1, Mar. 1986, pp. 18–25.

Zadeh, L. A., "Communication Fuzzy Algorithms", *Information and Control*, Academic Press Inc., vol. 12, No. 2, Feb. 1968, pp. 94–102.

Zadeh, L. A., "Fuzzy Sets", *Information and Control*, Academic Press Inc., vol. 8, No. 3, Jun. 1965, pp. 338–353.

Aoyama, T. et al., "Neural Networks Applied to Structure–Activity Relationships," *Journal of Medicinal Chemistry*, American Chemical Society, vol. 33., No. 3, 1990, pp. 905–908.

Gasteiger, J. et al., "Analysis of the Reactivity of Single Bonds in Aliphatic Molecules by Statistical and Pattern Recognition Methods," *Journal of Chemical Information and Computer Sciences*, American Chemical Society, vol. 33, No. 3, 1993, pp. 385–394.

Guez, A. and Nevo, I., "Neural networks and fuzzy logic in clinical laboratory computing with application to integrated monitoring," *Clinica Chimica Acta*, Elsevier Science Publishers B.V., vol. 248, 1996, pp. 73–90.

Rouvray, D.H., "Similarity in Chemistry: Past, Present and Future," *Topics in Chemistry*, Springer–Verlag, vol. 173, 1995, pp. 1–30.

de Ridder, D. and Duin, R.P.W., "Sammon's mapping using neural networks: A comparison," *Pattern Recognition Letters*, Elsevier Science Publishers B.V., vol. 18, No. 11–13, 1997, pp. 1307–1316.

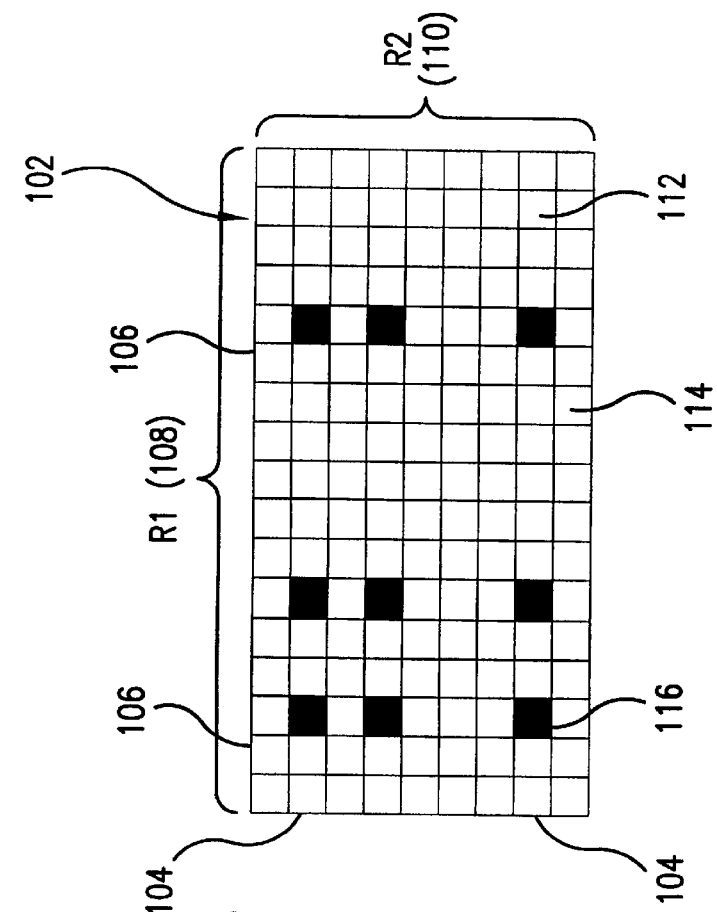
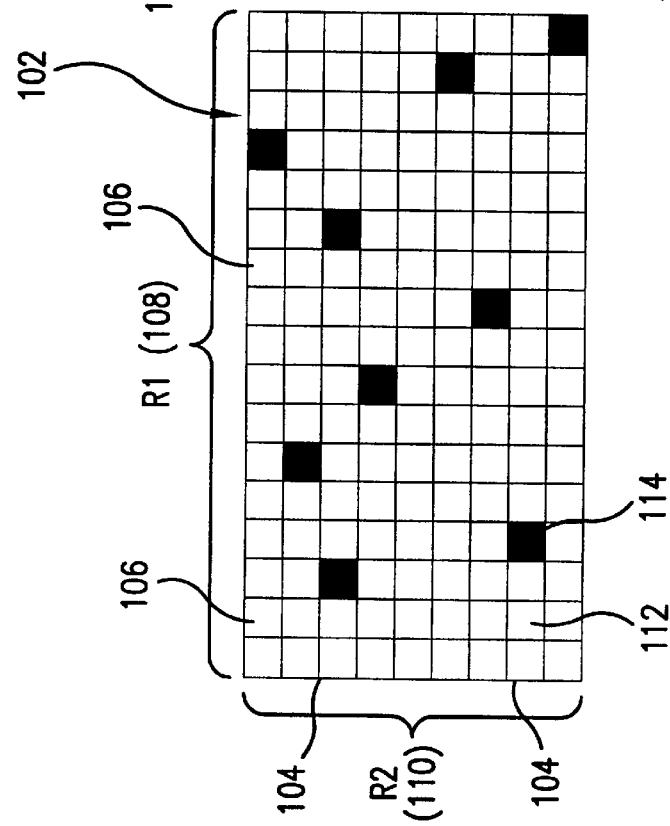
FIG.1A
FIG.1B

| R1 | R2 |
|---|---|
| 1 | 1 |
| 2 | 2 |
| 3 | 3 |
| 4 | 4 |
| 5 | 5 |
| 6 | 6 |
| 7 | 7 |
| 8 | 8 |
| 9 | 9 |
| 10 | 10 |

| R1 | R2 |
|---|---|
| 2 | 7 |
| 6 | 1 |
| 7 | 6 |
| 9 | 3 |
| 1 | 8 |
| 8 | 2 |
| 3 | 5 |
| 5 | 4 |
| 10 | 10 |
| 4 | 9 |

FIG.2D

| R1 | R2 |
|---|---|
| 3 | 7 |
| 1 | 1 |
| 10 | 6 |
| 2 | 3 |
| 4 | 8 |
| 8 | 2 |
| 5 | 5 |
| 7 | 4 |
| 9 | 10 |
| 6 | 9 |

| R1 | R2 |
|---|---|
| 3 | 6 |
| 1 | 10 |
| 10 | 4 |
| 2 | 9 |
| 4 | 8 |
| 8 | 5 |
| 5 | 1 |
| 7 | 3 |
| 9 | 7 |
| 6 | 2 |

FIG.2F

| R1 | R2 |
|---|---|
| 3 | 6 |
| 10 | 10 |
| 4 | 4 |
| 1 | 9 |
| 8 | 8 |
| 2 | 5 |
| 5 | 1 |
| 7 | 3 |
| 6 | 7 |
| 9 | 2 |

| R1 | R2 |
|---|---|
| 3 | 10 |
| 10 | 6 |
| 4 | 9 |
| 1 | 4 |
| 8 | 8 |
| 2 | 1 |
| 5 | 3 |
| 7 | 5 |
| 6 | 2 |
| 9 | 7 |

FIG.2H

METHOD AND COMPUTER PROGRAM PRODUCT FOR DESIGNING COMBINATORIAL ARRAYS

CROSS-REFERENCE TO RELATED APPLICATIONS

This application claims the benefit under 35 U.S.C. §119 (e) of U.S. Provisional application No. 60/185,700, filed Feb. 29, 2000, which is incorporated by reference herein in its entirety.

BACKGROUND OF THE INVENTION

1. Field of the Invention

The invention relates generally to the field of combinatorial chemistry and more particularly to a method and computer program product for designing combinatorial arrays.

2. Related Art

Historically, drug discovery has been based on a serial and systematic modification of chemical structure guided by the "similar property principle", i.e., the assumption that structurally similar compounds tend to exhibit similar physicochemical and biological properties. New therapeutic agents are typically generated by identifying a lead compound and creating variants of that compound in a systematic and directed fashion. The first phase of the process, known as lead generation, is carried out by random screening of large compound collections. Such compound selections may include, natural product libraries, corporate banks, etc. The second phase of the process, known as lead optimization, represents the rate-limiting step in drug discovery. This step involves the elaboration of sufficient structure-activity relationship (SAR) around a lead compound and the refinement of its pharmacological profile. Prior to the arrival of combinatorial chemistry, this process involved a simple prioritization of synthetic targets based on preexisting structure-activity data, synthetic feasibility, experience, and intuition.

Advances in synthetic and screening technology have recently enabled the simultaneous synthesis and biological evaluation of large chemical libraries containing hundreds to tens of thousands of compounds. With the expansion of the knowledge base of solid- and solution-phase chemistry and the continuous improvement of the underlying robotic hardware, combinatorial chemistry has moved beyond its traditional role as a source of compounds for mass screening and is now routinely employed in lead optimization and SAR refinement. This has led to the conceptual division of combinatorial libraries into (1) exploratory or universal libraries which are target-independent and are designed to span a wide range of physicochemical and structural characteristics and (2) focused or directed libraries which are biased toward a specific target, structural class, or known pharmacophore.

Two different methods are known for designing combinatorial experiments. The first is called "singles" or "sparse array" and refers to a subset of products that may or may not represent all possible combinations of a given set of reagents. The second is called a "full array" or simply "array" and represents all the products derived by combining a given subset of reagents in all possible combinations as prescribed by the reaction scheme.

The combinatorial nature of the two problems is vastly different. For singles, the number of possibilities that one has to consider (the number of different k-subsets of an n-set) is given by the binomial $$C_s = \frac{n!}{(n-k)!k!} \quad (1)$$

In contrast, the number of different $k_1 \times k_2 \times \ldots k_R$ arrays derived from an $n_1 \times n_2 \times \ldots n_R$ R-component combinatorial library is given by $$C_a = \prod_{i=1}^{R} \frac{n_i!}{(n_i - k_i)!k_i!} \quad (2)$$

For a 10×10 two-component combinatorial library, there are $10^{25}$ different subsets of 25 compounds (singles) and only 63,504 different 5×5 arrays. For a 100×100 library and a 100/10×10 selection, those numbers increase to $10^{241}$ and $10^{26}$ for singles and arrays, respectively. Note that in this context, the term "array" is basically equivalent to reagent selection based on the properties of the products and does not necessarily refer to the physical layout and execution of the experiment. Although arrays are generally inferior in terms of meeting the design objectives, they require fewer reagents and are much easier to synthesize in practice.

Conventional methods for generating combinatorial arrays include reagent-based methods, and product-based methods based on stochastic sampling. Reagent-based methods examine each variation site independently of the other sites in the combinatorial library. A variation site is a point on a combinatorial core that allows the introduction of multiple building blocks into the combinatorial structure. For example, in a two-component combinatorial library, the design is carried out by selecting a list of reagents exhibiting certain desired properties from R1 and a list of reagents exhibiting certain desired properties from R2. Then the selected reagents from R1 are combined with the selected reagents from R2 to produce a list of products, which constitute the combinatorial array. Although this method simplifies the selection process by examining each reagent pool independently of all the others, the properties of the products, which are of most concern, are never explicitly considered. Instead, this method is based on the hope that the selected reagents will result in a list of products that possess the desired properties.

The selection of reagents based on the properties of the products is conventionally accomplished using algorithms that are stochastic in nature. For example, in a two-component combinatorial library, a number of reagents from both R1 and R2 are randomly selected. The selected reagents from R1 are combined with the selected reagents from R2. The resulting products are evaluated against some design objective. For example, if the design objective is to obtain products that are similar in nature to a known drug molecule, then the products are evaluated based on their similarity to that known drug molecule, resulting in some numerical value. Then one of the selected reagents at one of the variation sites is chosen at random and is replaced by another randomly chosen reagent from the pool of candidate reagents at that site. Better or worse results may occur. This process is repeated until some convergence criterion or time limit is met, for example until the resulting similarity values to the known drug molecule can no longer be improved. Thus, stochastic sampling methods require a significant amount of trials until a satisfactory solution is obtained.

What is needed is an algorithm for designing combinatorial arrays that capitalizes on the presence of optimal substructure when the objective function is decomposable or nearly decomposable to individual molecular contributions and allows the selection of optimal or nearly optimal arrays in an expedient fashion. What is further needed is a method for designing combinatorial arrays based on similarity to one or more reference compounds, or predicted activity and/or selectivity against one or more biological targets according to one or more QSAR, pharmacophore, or receptor binding models, degree of matching against one or more queries or probes, containment within certain property bounds, etc.

SUMMARY OF THE INVENTION

The present invention solves the above stated problem by providing a greedy method and computer program product for designing combinatorial arrays. The greedy method is particularly well suited in situations where the objective function is decomposable or nearly decomposable to individual molecular contributions. The invention makes use of a heuristic that allows the independent evaluation and ranking of candidate reagents in each variation site in a combinatorial library. The greedy method, when executed, is convergent and produces combinatorial arrays in an expedient manner. The combinatorial array solutions produced by the greedy method are comparable to, and often better than, those derived from the substantially more elaborate and computationally intensive stochastic sampling techniques. Typical examples of design objectives that are amendable to this approach include similarity to one or more reference compounds, predicted activity or selectivity according to one or more structure-activity or receptor binding models, degree of matching to one or more queries or probes, containment within certain molecular property bounds, and many others.

According to the greedy method of the present invention, an array of reagents from a combinatorial library is initialized at random or by some other technique, and its fitness (i.e. the degree to which it satisfies the design objectives) is evaluated. This initial selection is refined in an iterative fashion by processing the reagent lists in each variation site of the combinatorial library in a strictly alternating sequence. During each step, each sub-array resulting from the combination of each of the candidate reagents at the variation site under investigation with the selected reagents at the remaining sites of the library is evaluated, and their fitness is recorded. The candidate reagents that produce the best (most fit) sub-arrays are then selected for that site, and the next site is processed in a similar fashion. The process terminates when the fitness of the resulting combinatorial array can no longer be improved. The process may be repeated a number of times, each time starting from a different initial array. This process is ideally suited in situations where the fitness function is decomposable or nearly decomposable to individual molecular contributions.

Further features and advantages of the present invention, as well as the structure and operation of various embodiments of the present invention, are described in detail below with reference to the accompanying drawings. In the drawings, like reference numbers indicate identical and/or functionally similar elements. Also, the leftmost digit(s) of the reference numbers identify the drawings in which the associated elements are first introduced.

BRIEF DESCRIPTION OF THE DRAWINGS/ FIGURES

The accompanying drawings, which are incorporated herein and form part of the specification, illustrate the present invention and, together with the description, further serve to explain the principles of the invention and to enable a person skilled in the pertinent art to make and use the invention.

FIG. 1A is a diagram illustrating the selection of compounds from a hypothetical two-component combinatorial library in singles (sparse array) format.

FIG. 1B is a diagram illustrating the selection of compounds from a hypothetical two-component combinatorial library in (full) array format.

FIGS. 2C–2H are simplified examples of iterations of the greedy method for the selection of a 3×2 array from a 10×10 combinatorial library.

Figure 2A:
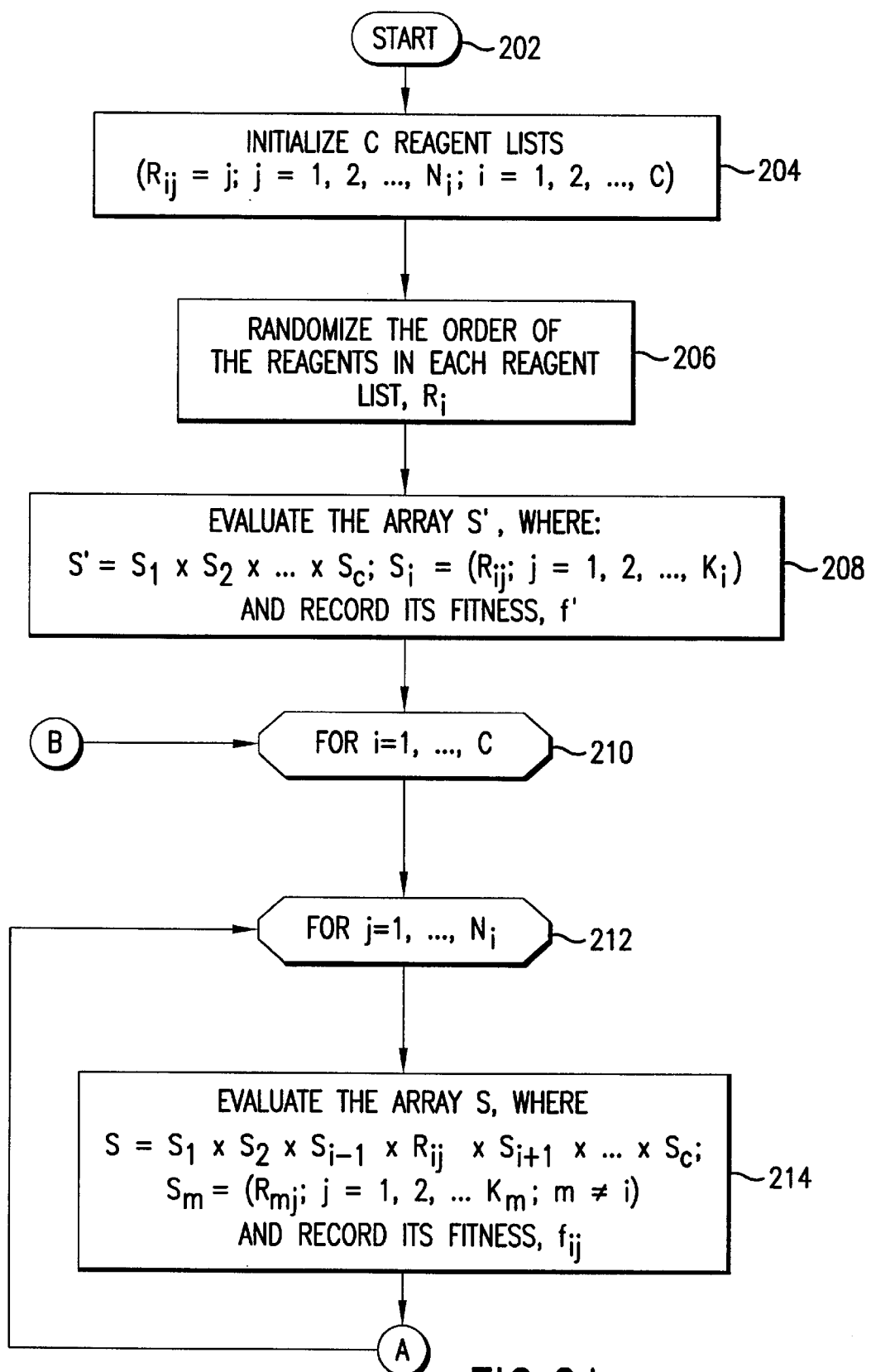
FIGS. 2A and 2B are a flow diagram of a method for producing combinatorial arrays.

The features, objects, and advantages of the present invention will become more apparent from the detailed description set forth below when taken in conjunction with the drawings in which like reference characters identify corresponding elements throughout. In the drawings, like reference numbers generally indicate identical, functionally similar, and/or structurally similar elements. The drawings in which an element first appears is indicated by the leftmost digit(s) in the corresponding reference number.

DETAILED DESCRIPTION OF THE INVENTION

While the present invention is described herein with reference to illustrative embodiments for particular applications, it should be understood that the invention is not limited thereto. Those skilled in the art with access to the teachings provided herein will recognize additional modifications, applications, and embodiments within the scope thereof and additional fields in which the present invention would be of significant utility.

Overview

The present invention is a method and computer program product for designing combinatorial arrays. In particular, the present invention is a method and computer program product for selecting a subset of reagents for one or more variation sites of a combinatorial library from a pool of reagents available at that site, in a way that satisfies one or more design objectives to a significant extent. The method of the present invention is applicable when the objective function (i.e. the function that measures the degree to which a particular selection of compounds satisfies the design objective(s)) is decomposable or nearly decomposable to individual molecular contributions. The invention makes use of a heuristic that allows the independent evaluation and ranking of candidate reagents in each variation site in a combinatorial library. The method is extremely fast and convergent. The solutions produced from employing the method of the present invention are comparable to and often better than those derived from the substantially more elaborate and computationally intensive stochastic sampling techniques described above. Example design objectives that are amendable to this approach include, but are not limited to, similarity to one or more reference structures, predicted activity or selectivity according to one or more structure-activity or receptor binding models, degree of matching against one or more queries or probes, containment within certain molecular property bounds, and many others.

Two known methods for designing combinatorial experiments are "singles" (also referred to as "sparse arrays") and "full arrays" (or simply "arrays"). Singles refers to a subset of products that may or may not represent all possible combinations of a given set of reagents. Full arrays represent all the products derived by combining a given subset of reagents in all possible combinations as prescribed by a reaction scheme.

FIG. 1A is a diagram illustrating the selection of compounds from a hypothetical two-component combinatorial library in singles format. A grid 102 represents a virtual library. The main use of virtual libraries is to enable the selection of smaller sub-libraries for physical synthesis and/or testing.

Grid 102 is comprised of nine (9) rows 104 and seventeen (17) columns 106.

Although a grid size of 9×17 is used in FIG. 1A, this is for exemplary purposes only. One skilled in the art would know that virtual libraries may be larger or smaller in size without departing from the scope of the present invention. Every column 106 represents a different reagent, R1, for a first site 108. For example, each reagent R1 represents a different aldehyde. Every row 104 is a different reagent, R2, for a second site 110. For example, each reagent R2 represents a different amine. Every cell 112 of grid 102 represents a different product that results from, for example, the combination of a particular amine R2 with a particular aldehyde R1.

In this example, nine (9) compounds are selected using the singles method. The nine (9) compounds are shown as a darkened cell 114. The singles selection of compounds span nine (9) columns and eight (8) rows. Thus, the selected compounds use nine different aldehydes and eight different amines. Using a singles method for designing combinatorial experiments not only requires a large number of possibilities to consider, but also requires a large number of reagents to be used. Regardless of whether the synthesis is carried out manually or robotically, synthesis of compounds in singles format is usually laborious and time consuming. While this method retrieves the best possible hits with regard to one's design objectives, it almost always results in experiments that are extremely difficult and expensive to execute.

Thus, to contain costs and simplify synthesis, combinatorial libraries are usually synthesized in array format, even though arrays are generally inferior in terms of meeting the primary design objectives. FIG. 1B is a diagram illustrating the selection of compounds from a hypothetical two-component combinatorial library in array format. Nine (9) compounds are selected using the array method. The nine (9) compounds are shown as a darkened cell 116. The array selection of compounds span three (3) columns and three (3) rows. In contrast to the singles method for designing combinatorial experiments, the array method uses only three (3) different aldehydes and three different amines, and therefore, results in fewer reagents being used. Regardless of whether the synthesis is carried out manually or robotically, synthesis of compounds in array format is usually easier to execute. The method of the present invention is used to select an array that meets a set of design objectives to a significant extent among all possible arrays from the combinatorial library.

Design Objectives

For exemplary purposes, three types of design objectives or selection criteria are considered. They are: (1) maximum similarity to a given lead or set of leads (similarity), (2) maximum fit to a prescribed set of property constraints (confinement), and (3) maximum activity and/or selectivity against a particular biological target (activity/selectivity). Although only three design objectives are described, the invention is not limited to these three design objectives. Other design objectives that are decomposable or nearly decomposable to individual molecular contributions may be used as well. In an embodiment, each of the design objectives may be used individually and/or in combination with one another.

Similarity

The similarity of a given set of compounds, C, to a set of leads is defined as the average distance of a compound to its nearest lead:

$$S(C) = \frac{1}{N} \sum_{i=1}^{N} \min_{j=1}^{L}(d_{ij}) \tag{3}$$

where N is the cardinality of C, L is the number of leads, and $d_{ij}$ is the distance between the ith compound and the jth lead in some molecular descriptor space. A higher similarity score indicates a collection of compounds that are more distant and therefore less similar to the leads. Thus, focused libraries are obtained by minimizing S. If the number of leads is large, the innermost loop in Eq. 3 can be carried out using a k-d tree algorithm as described in D. K. Agrafiotis et al., 39 J. Chem. Inf. Computer Sci., 51–8 (1999), which is incorporated herein by reference in its entirety.

Confinement

This design objective measures the degree to which the properties of a given set of compounds fit within prescribed limits, and is defined as:

$$P(C) = \frac{1}{N} \sum_{i} \sum_{j} \max(x_j^{min} - x_{ij}, x_{ij} - x_j^{max}, 0) \tag{4}$$

where $x_{ij}$ is the jth property of the ith compound, and $x_j^{min}$ and $x_j^{max}$ are the minimum and maximum allowed limits of the jth property, respectively. The value of this function increases as more and more compounds fall outside the desired property range. Thus, constrained libraries are obtained by minimizing P. In an embodiment where multiple properties are used, the properties must be normalized or weighed to allow meaningful comparisons. In an embodiment where the properties of interest need to attain a particular target value (i.e., in the case of a degenerate range), Eq. 4 can be rewritten as:

$$P(C) = \frac{1}{N} \sum_{i} \sum_{j} abs(x_{ij} - x_j^*) \tag{5}$$

where $x_j^*$ represents the target value of the jth property.

Activity/Selectivity

A common goal in library design is to produce arrays of compounds that are predicted to be maximally active against a predefined target according to some quantitative structure-activity or receptor binding model. This is accomplished by expressing the predicted activity of a given set of compounds, C, as the sum of the predicted activities of the individual compounds:

$$Q_A(C) = \frac{1}{N} \sum_{i} a_i \tag{6}$$

where $\alpha_i$ is some measure of the predicted activity of the ith compound in C. A similar function can be used to measure the selectivity against a set of biological targets:

$$Q_S(C) = \frac{1}{N} \sum_{i} \left( a_{ik} - \max_{j \neq k}(a_{ij}) \right)$$

where $\alpha_{ij}$ is the predicted activity of the ith compound against the jth target, and k is the target that the molecules should be selective against. The value of $Q_A/Q_S$ increases as the compounds become more active/selective. Thus, active/selective libraries are obtained by maximizing the respective criterion.

Multi-Objective Design

In an embodiment, individual design objectives, such as, but not limited to, the design objectives previously described, can be combined to produce arrays that satisfy multiple design objectives. This results in a multi-objective fitness function defined as:

$$F(C)=f(F_1(C), F_2(C), \dots) \tag{8}$$

where F(C) is the overall performance measure, and $F_i(C)$ are individual criteria associated with the collection C. The exact form of this function and the coefficients associated with the individual design objectives determine the influence of each design objective in the final selection.

The Greedy Method of the Present Invention

As previously stated, the present invention is most applicable in situations where the objective function is described as the sum of individual molecular contributions. The invention allows the selection of optimal or nearly optimal arrays in an expedient fashion. The invention employs the following optimization heuristic. Given a combinatorial library of C components, a position I∈[1, C], and a particular choice of reagents for $R_{j \neq i}$, j =1,2, . . . , i−1, i+1,. . .,C, the reagents for $R_i$ that maximize the objective function can be determined by constructing and evaluating all possible sub-arrays derived from the combination of a single reagent from $R_i$ with all the selected reagents for $R_{j \neq i}$, and selecting the ones with the best fitness (i.e. the degree to which they satisfy the design objective(s)). The process starts with a randomly chosen array, and optimizes each site in sequence until no further improvement is possible.

For example, consider the selection of a 5×5×5 array from a 10×10×10 combinatorial library. The process begins by selecting five (5) reagents at random from each site and evaluating the fitness of the resulting array. This initial selection is refined in an iterative fashion by processing each reagent list in a strictly alternating sequence. First, ten (10) 1×5×5 sub-arrays are constructed by combining each reagent from $R_1$ with the selected reagents from $R_2$ and $R_3$. The resulting combinations or products are evaluated against the design objective(s) to determine their fitness. Every reagent at $R_1$ is evaluated in turn, and the five (5) reagents from $R_1$ with the highest score are selected. The process is then repeated for $R_2$. Each reagent in $R_2$ is used to construct a 5×1×5 sub-array derived by combining it with the selected reagents from $R_1$ and $R_3$, and the five (5) $R_2$ reagents resulting in the best fitness are selected for that site. $R_3$ is then processed in a similar fashion, and this completes one refinement cycle. Once all the reagent lists have been processed, the selected reagents from each site are combined, and the fitness of the resulting full array is evaluated and compared to the fitness of the selection at the end of the previous cycle. If the fitness is improved, the refinement process is repeated starting at $R_1$. If not, the process terminates.

Figure 2B:
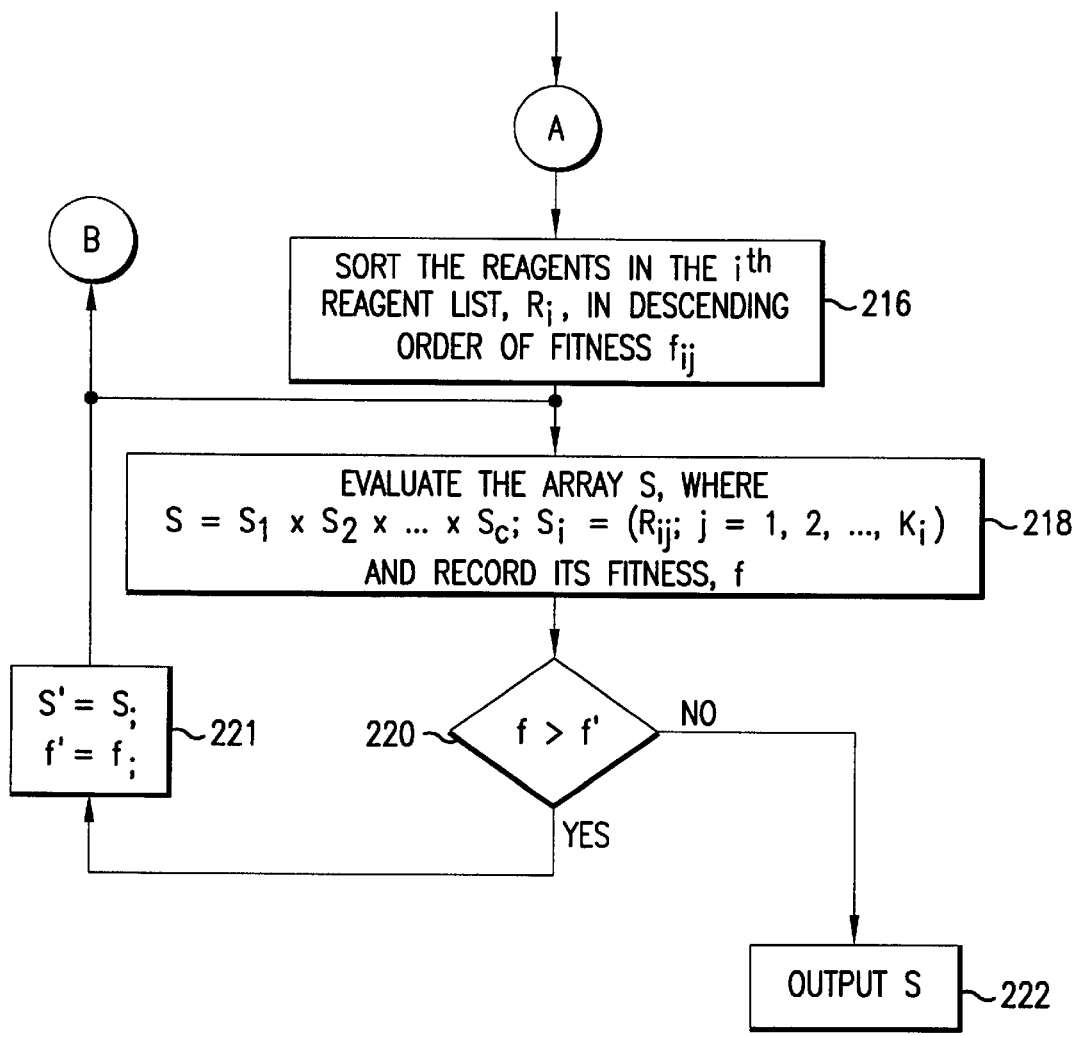

FIGS. 2A and 2B are a flow diagram of a method for producing combinatorial arrays. The number of substitution sites in the combinatorial library is represented as C. The total number of reagents and the size of the requested array at the i-th position are represented as $N_i$ and $K_i$, respectively.

Beginning with FIG. 2A, the process begins with step 202, where the process immediately proceeds to step 204.

In step 204, the reagent lists are initialized $\{R_{ij}=j; j=1,2,\ldots,N_i; i=1,2,\ldots,C\}$. The number of reagent lists is equal to the number of substitution sites in the combinatorial library, C. The process proceeds to step 206.

In step 206, the order of the reagents in each reagent list, $R_i$, is randomized.

In step 208, the fitness of the resulting array is evaluated and recorded.

The process then proceeds to step 210.

In step 210, the iterative process begins for processing each reagent list in a strictly alternating sequence.

In step 212, an inner iterative loop begins for processing each reagent from the reagent list identified in step 210.

In step 214, subarrays are derived by combining the reagent identified in step 212 from the reagent list identified in step 210 with the selected reagents from the other sites and evaluated for fitness. The process then proceeds back to step 212 to evaluate the next reagent from the reagent list identified in step 210. Every reagent in the identified reagent list is evaluated in turn in step 214. When all reagents in the identified reagent list have been evaluated, the process proceeds to step 216 in FIG. 2B.

In step 216, the reagents with the best fitness are selected. This step requires the reordering of the reagents in the reagent list identified by step 210 in descending order of fitness, with the best fit reagents listed at the top of the reagent list. The process then proceeds back to step 210 in FIG. 2A to restart the iterative process for the next reagent list. Steps 212–216 are repeated for each reagent list. When all of the reagent lists have been processed, a refinement cycle is completed. At the completion of a refinement cycle, the process then proceeds to step 218.

In step 218, the selected reagents from each site are combined and the fitness of the resulting full array is evaluated. The process then proceeds to decision step 220.

In decision step 220, the fitness of the resulting full array is compared to the fitness of the selection at the end of the previous cycle. If the fitness of the resulting full array is greater than the fitness of the selection at the end of the previous cycle, the fitness has improved. The present fitness is identified as the previous fitness for the next refinement cycle in step 221. The process then proceeds back to step 210 in FIG. 2A to perform another refinement cycle.

Returning back to decision step 220 in FIG. 2B, if the fitness of the resulting full array is less than or equal to the fitness of the selection at the end of the previous cycle, the fitness has not improved and the process proceeds to step 222.

In step 222, the resulting combinatorial array is provided as output, and the process ends.

To minimize the computational effort required, one embodiment of the greedy method precomputes the individual contribution to the objective function for each compound in the entire library and stores it in a working array. This step is carried out once and is of O(N). During the optimization, the fitness of any given array or sub-array is evaluated by simply adding the precomputed individual contributions of the molecules that make up the array.

Occasionally, the greedy method may get trapped into a local minimum. For this reason, the process may be repeated a few times starting from a different random seed (i.e., a different, randomly chosen, starting array), and the selection with the best fitness is reported. In an alternative embodiment with minor modifications, the greedy method can be used to select smaller sub-arrays from within larger arrays of a given virtual library. In another embodiment, one or more of the reagents comprising the final array may be pre-selected. In this case, the greedy algorithm attempts to fill the combinatorial array, i.e. identify which reagents need to be added to the pre-selected reagents in order to produce an optimal or nearly optimal array.

FIGS. 2C–2H are simplified examples of iterations of the greedy method for the selection of a 3×3 array from a 10×10 combinatorial library.

FIG. 2C shows the initial rankings of the reagents in reagent lists R1 and R2.

FIG. 2D shows the order of the reagents in reagent lists R1 and R2 after randomization of the order of the reagents. The fitness for this array was determined to be a value of 6.

FIG. 2E shows the order of the reagents in reagent lists R1 and R2 after the top three (3) reagents in R2 have been combined with each of the reagents in R1, the combinations evaluated for fitness, and the reagents in R1 resorted accordingly.

FIG. 2F shows the order of the reagents in reagent lists R1 and R2 after the top three (3) reagents in R1 have been combined with each of the reagents in R2, the combinations evaluated for fitness, and the reagents in R2 resorted accordingly. This completes a refinement cycle. The fitness for the resulting 3×3 array is determined to be 8. Since 8 is greater than 6, the process must be repeated, and the new previous fitness value is set to 8.

FIG. 2G shows the order of the reagents in reagent lists R1 and R2 after the top three (3) reagents in R2 have been combined with each of the reagents in R1, the combinations evaluated for fitness, and the reagents in R1 resorted accordingly.

FIG. 2H shows the order of the reagents in reagent lists R1 and R2 after the top three (3) reagents in R1 have been combined with each of the reagents in R2, the combinations evaluated for fitness, and the reagents in R2 resorted accordingly. This completes another refinement cycle. The fitness for the resulting full array is determined to be 8. Since the new fitness value of 8 is no greater than the previous fitness value of 8, the resulting full array is output and the process ends.

Application of the Greedy Method for Providing Combinatorial Arrays

To test the effectiveness of the greedy method, a simulated annealing method was used for comparison purposes. The simulated annealing method has been found to be very effective in the design of combinatorial libraries. The simulated annealing method involves two main components: a search engine and an objective function. The search engine produces a list of k compounds from a virtual collection (also referred to as a state), which is subsequently evaluated by an objective function to produce a numerical estimate of its quality or fitness. The objective function encodes the design objectives of the experiment, such as the intrinsic diversity of the compounds or their similarity to a predefined set of leads. This fitness value is fed back to the search engine which modifies the state in a controlled manner and produces a new list of compounds, which are, in turn, evaluated against the design objective criteria in the manner described above. This process is repeated until no further improvement is possible, or until some predetermined convergence criterion or time limit is met. In the case at hand, the selection was carried out in 30 temperature cycles, using 1,000 sampling steps per cycle, a Gaussian cooling schedule, and the Metropolis acceptance criterion (p= $e^{-\Delta E/K_B T}$), all of which are well known to a person skilled in the relevant art(s). For array selections, a step represents the substitution of a single reagent in the combinatorial array. Boltzmann's "constant", $K_B$, was adjusted in an adaptive manner, by constantly updating the mean transition energy during the course of the simulation, and continuously adjusting the value of $K_B$ so that the acceptance probability for a mean uphill transition at the final temperature was 0.001. Details of this algorithm can be found in D. K. Agrafiotis, *J. Chem. Inf Computer Sci.*, 576–90, 841–51 (1997), which is incorporated herein by reference in its entirety.

Data Sets

Figure 3:
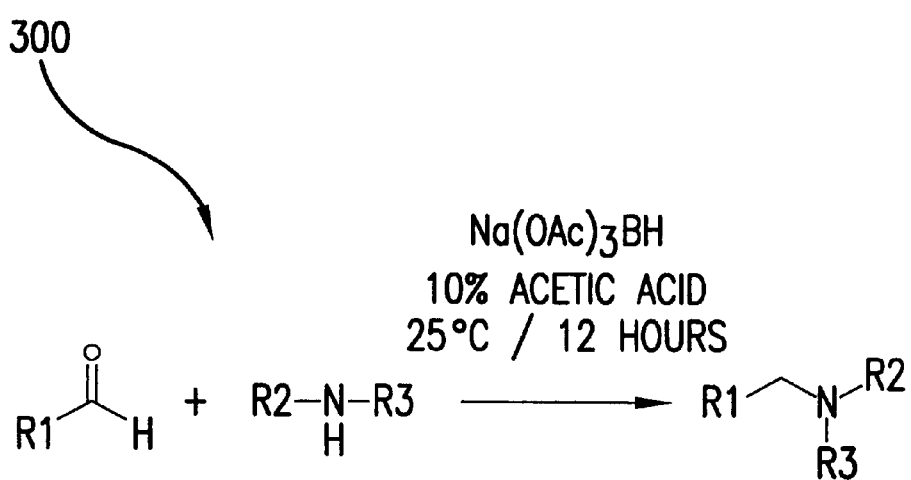
FIG. 3 is a diagram illustrating the synthetic sequence for the reductive amination library.

Two data sets were used to test the effectiveness of the present invention. The first data set is a 2-component combinatorial library based on the reductive amination reaction. A synthetic sequence 300 for the reductive amination library is illustrated in FIG. 3. The reaction is carried out by adding a solution of primary or secondary amine to an equimolar ratio of aldehyde in 1,2-dichloroethane/N,N-dimethyl formamide. Sodium triacetoxyborohydride (2 equivalents) in 10% acetic acid/DMF is added to the reaction vial. Stirring of the reaction mixture at 25° C. for 12 hours and subsequent addition of methanol followed by concentration yields the product in high purity.

A set of 300 amines with 300 aldehydes were selected at random from the Available Chemicals Directory, which is marketed by MDL Information Systems, Inc., in San Leandro, Calif., and were used to generate a virtual library of 90,000 products using the library enumeration classes of the DirectedDiversity® toolkit. The DirectedDiversity® toolkit is copyrighted by 3-Dimensional Pharmaceuticals, Inc., Exton, Pa. (1994–2000), and is incorporated herein by reference in its entirety. These enumeration classes take as input lists of reagents supplied in SDF or SMILES format, and a reaction scheme written in a proprietary language that is based on SMARTS and an extension of the scripting language Tcl.

Each compound in the 90,000-membered library was characterized by a standard set of 117 topological descriptors computed with the DirectedDiversity® toolkit. These descriptors include an established set of topological indices with a long, successful history in structure-activity correlation such as molecular connectivity indices, kappa shape indices, subgraph counts, information-theoretic indices, Bonchev-Trinajstis indices, and topological state indices. See L. H. Hall et al., *The Molecular Connectivity Chi Indexes and Kappa Shape Indexes in Structure-Property Relations*, Reviews of Computational Chemistry; D. B. Boyd et al., Eds.; VCH: Weinheim, Germany (1991); Chapter 9, pp. 367–422, incorporated herein by reference in its entirety. See also D. Bonchev et al., 67 *J. Chem. Phys.,* 4517–33 (1977), incorporated herein by reference in its entirety. These descriptors exhibit proper "neighborhood behavior" (as defined in D. E. Patterson et al., 39 *J. Med. Chem.,* 3049–59 (1996), which is incorporated herein by reference in its entirety) and are thus well suited for diversity analysis and similarity searching. See V. S. Lobanov et al., 40 *J. Chem. Inf Computer Sci.,* 460–70 (2000), which is incorporated herein by reference in its entirety.

These 117 molecular descriptors were subsequently normalized and decorrelated using principal component analysis, which is well known to those skilled in the relevant art(s). This process resulted in an orthogonal set of 23 latent variables, which accounted for 99% of the total variance in the data. To simplify the analysis and interpretation of results, this 23-dimensional data set was further reduced to 2 dimensions using a very fast nonlinear mapping algorithm, as described in D. K. Agrafiotis et al., *J. Chem. Inf. Computer Sci.,* 40, 1356–1362 (2000), D. N. Rassokhin et al., *J. Comput. Chem.,* 22(4), 373–386 (2001), and D. K. Agrafiotis et al., *J. Comput. Chem.,* 22(5), 488–500 (2001), which are all incorporated herein by reference in their entireties. The projection was carried out in such a way that the pair-wise distances between points in the 23-dimensional principal component space were preserved as much as possible on the 2-dimensional map. The resulting map had a Kruskal stress of 0.187 and was used to visualize the selections, which were all carried out in the full 23-dimensional principal component space. The PCA preprocessing step was necessary in order to eliminate duplication and redundancy in the data, which is typical of graph-theoretic descriptors.

Finally, in addition to the 117 topological descriptors, the molecular weight and octanol-water partition coefficient (log P) of each compound was computed independently using the Ghose-Crippen approach, described in A. K. Ghose et al., 102 *J. Phys. Chem. A,* 3762–72 (1998), which is incorporated herein by reference in its entirety, as implemented in the DirectedDiversity® toolkit, and were used as the target variables for all constrained designs. This parameter was not included in the descriptor set used for similarity assessment. All selections were carried out as 10×10 arrays.

Figure 4:
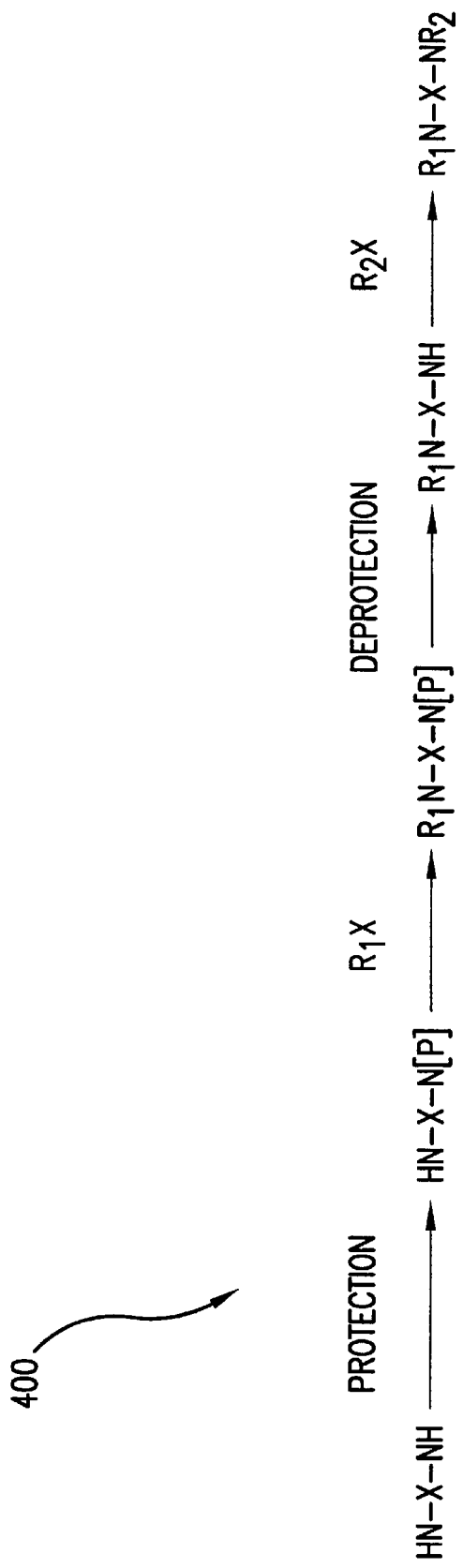
FIG. 4 is a diagram illustrating a synthetic sequence used to construct a diamine library.

The second example is a 3-component library taken from the work of Cramer et al., 38 *J. Chem. Inf Computer Sci.,* 1010–23 (1998), which is incorporated herein by reference in its entirety. A diamine molecule containing two primary or secondary amines served as the central scaffold, and was derivatized on both sides using an acylating agent, reactive halide or carbonyl group susceptible to reductive amination. The synthetic sequence required to generate this library involves selective protection of one of the amines and introduction of the first side chain, followed by deprotection and introduction of the second side chain. FIG. 4 is a diagram illustrating the synthetic sequence 400 used to construct the diamine library. Use of commercially available reagents alone (the 1996 Available Chemical Directory contained 1750 reagents of type HNXNH and 26,700 reagents of type RX) would yield over $10^{12}$ potential products. Since the objective of this work was to validate the array selection method, a small library comprised of 125,000 compounds using 50 commercially available diamines and 50 acid chlorides and alkylating agents was generated. As with the previous data set, each compound was described by 117 topological indices designed to capture the essential features of the molecular graph, which were subsequently decorrelated to 22 principal components, accounting for 99% of the total variance in the data. These principal components were used as input to a nonlinear dimensionality reduction technique to generate a 2-dimensional map that reproduced the pairwise distances of the compounds in the principal component space to a Kruskal stress of 0.167. This map was only used to visualize the designs, which were each based on all 22 decorrelated descriptors. Selections were carried out as 5×5×5 arrays.

Results and Discussion

The combinatorial nature of the problem does not permit an exhaustive enumeration of every possible array in either one of these collections. For the reductive amination library, the number of different 10×10 arrays as determined by Eq. 2 is $\sim 2 \cdot 10^{36}$, while for the diamine library the number of different 5×5×5 arrays is $\sim 2 \cdot 10^{19}$. In the absence of a known global minimum, three reference points were used to assess the quality of the solutions produced by the method of the present invention. The first is the fitness of a singles selection of an equivalent number of compounds, and represents the upper bound of the objective function for a given selection size. Since an array is a singles selection with additional constraints, it can never exceed the quality of a pure singles design. The singles are selected in a deterministic manner by evaluating the similarity of each compound to its nearest lead, sorting the compounds in descending order of similarity, and selecting the k top-most compounds from that list. The other two reference points are the average fitness of a random array and the fitness of the array derived from the annealing optimization method described above.

Figure 5:
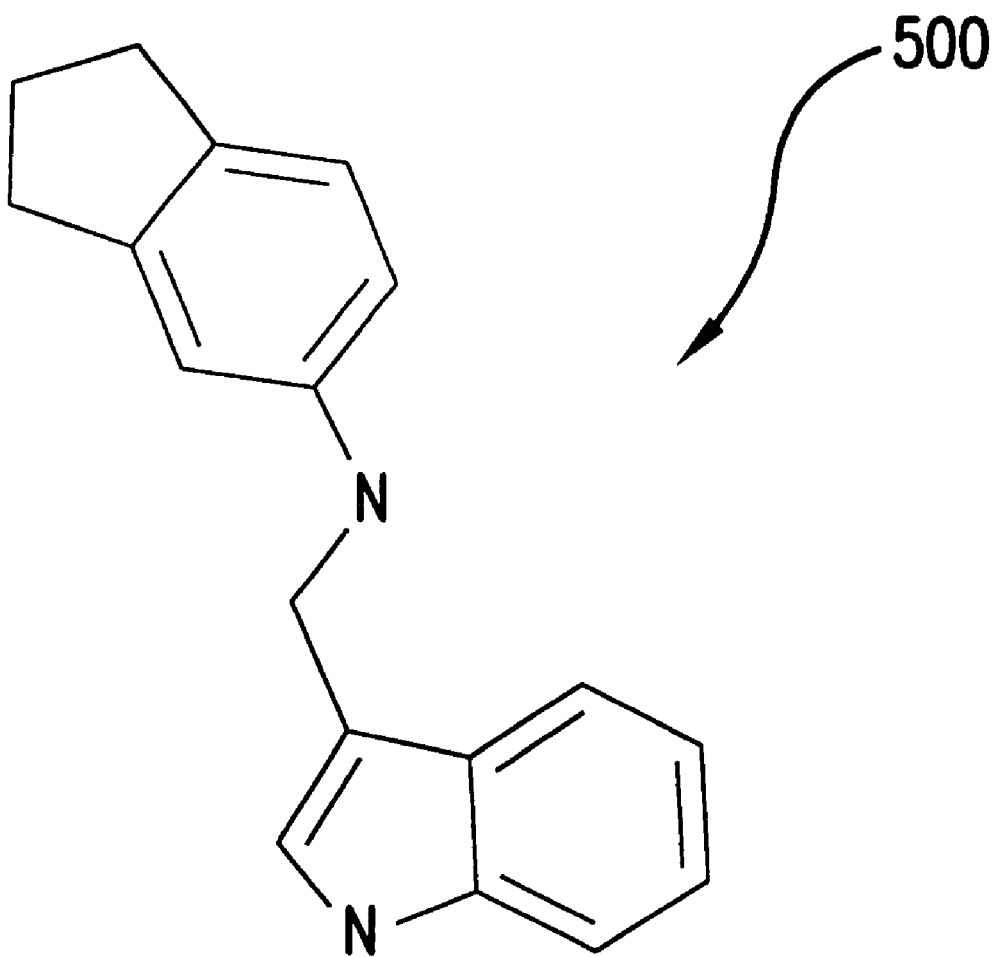
FIG. 5 is a diagram illustrating a reference structure used for similarity selections from the reductive amination library.

For the reductive amination library, the similarity selections were limited to 100 compounds (100 singles, 10×10 arrays) and were carried out using the similarity fitness function in Eq. 3 and a randomly chosen member of that library as a "lead." FIG. 5 is a diagram illustrating a reference structure 500 used for similarity selections from the reductive amination library. Since none of the methods are completely deterministic, the selections were repeated 100 times, each time starting from a different random initial configuration (random seed).

Figure 6:
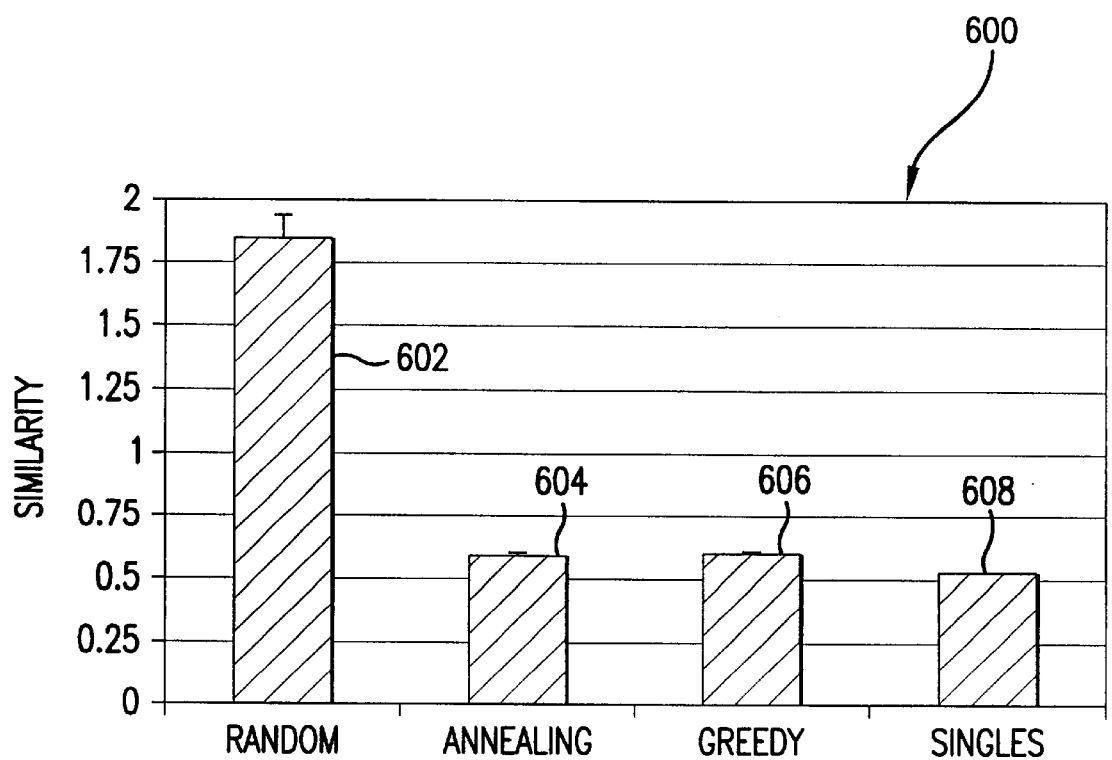
FIG. 6 is a bar graph illustrating the mean and standard deviations of similarity scores of 100 compounds selected from a reductive amination library according to maximum similarity to a reference structure.

FIG. 6 is a bar graph 600 illustrating the mean and standard deviations of the similarity scores of 100 compounds selected from the reductive amination library according to maximum similarity to reference structure 500.

Bar graph 600 shows results for a random or chance method 602, an annealing method 604, greedy method 606, and singles 608. The greedy method 606 proved to be superbly convergent: every single run produced the same solution which had a score of 0.594 and was the best among all the arrays discovered in this exercise. In contrast, simulated annealing 604 converged to that solution in only 60 out of 100 trials, although in general its performance was satisfactory with 82% and 98% of the trials leading to scores less than 0.60 and 0.61, respectively, and an overall average of 0.597±0.004. These solutions are considerably better than those obtained by chance 602 (the average score of a random array was 1.855±0.086), and compare very favorably to singles 608, which had a score of 0.533.

Figure 7A:
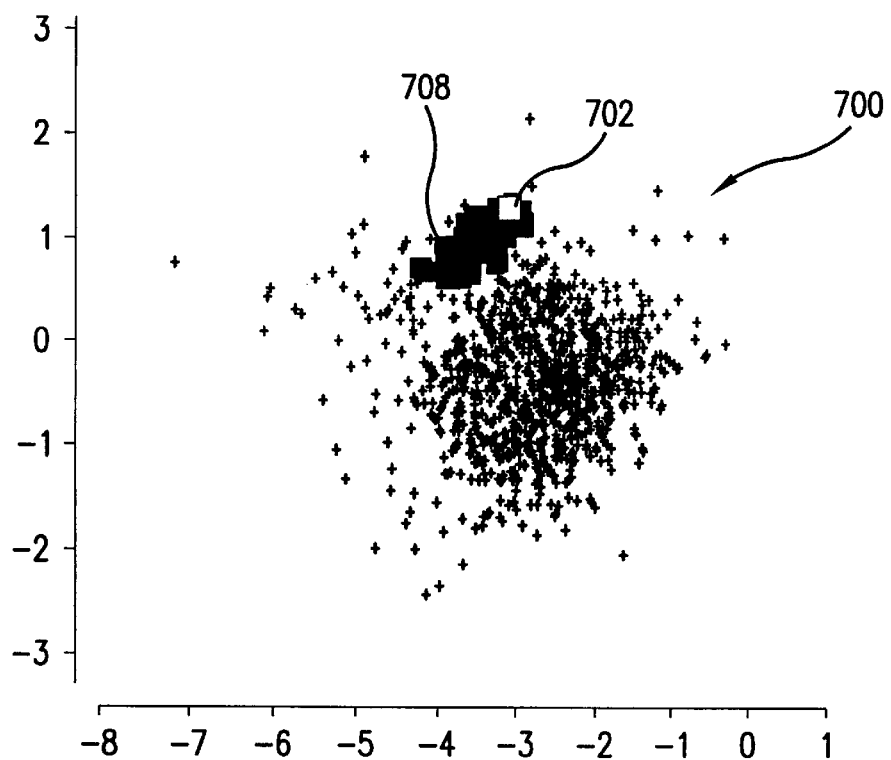
FIG. 7A is a graph illustrating the distribution of selected compounds from a reductive amination library according to a maximum similarity to a reference structure for a 10×10 array.
Figure 7B:
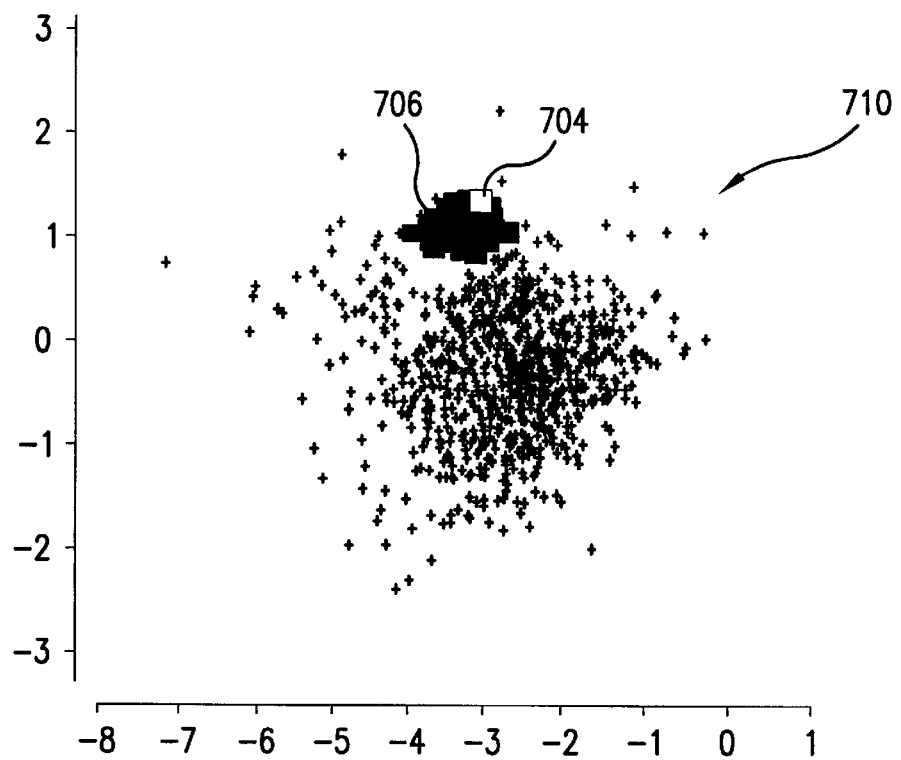
FIG. 7B is a graph illustrating the distribution of the selected compounds from the reductive amination library according to a maximum similarity to a reference structure for 100 singles.

FIG. 7A is a graph 700 illustrating the distribution of the selected compounds from the reductive amination library according to a maximum similarity to reference structure 500 for the 10×10 array. FIG. 7B is a graph 710 illustrating the distribution of the selected compounds from the reductive amination library according to a maximum similarity to reference structure 500 for 100 singles. FIG. 7B is used as a reference. The large square (702 and 704 in FIGS. 7A and 7B, respectively) represents the reference compound (lead), and the smaller squares (708 and 706 in FIGS. 7A and 7B, respectively) represent the selected compounds, respectively. The graphs in FIGS. 7A and 7B are two-dimensional nonlinear projections of the 23 principal components that accounted for 99% of the total variance in the data, constructed in a way that preserved the proximities (similarities) of the objects as faithfully as possible. The selection is based on all 23 principal components and is simply highlighted on this map. There is an inevitable distortion associated with this drastic reduction in dimensionality, and this is manifested by the presence of compounds that appear to be closer to the lead than the ones selected. However, with nonlinear mapping this distortion is distributed across the entire data space, and consequently even the relatively small differences between the singles and the array are clearly evident on the map. The actual selection consists mostly of various heterocyclic analogues of the fused ring system found in both side chains of the lead compound.

Figure 8:
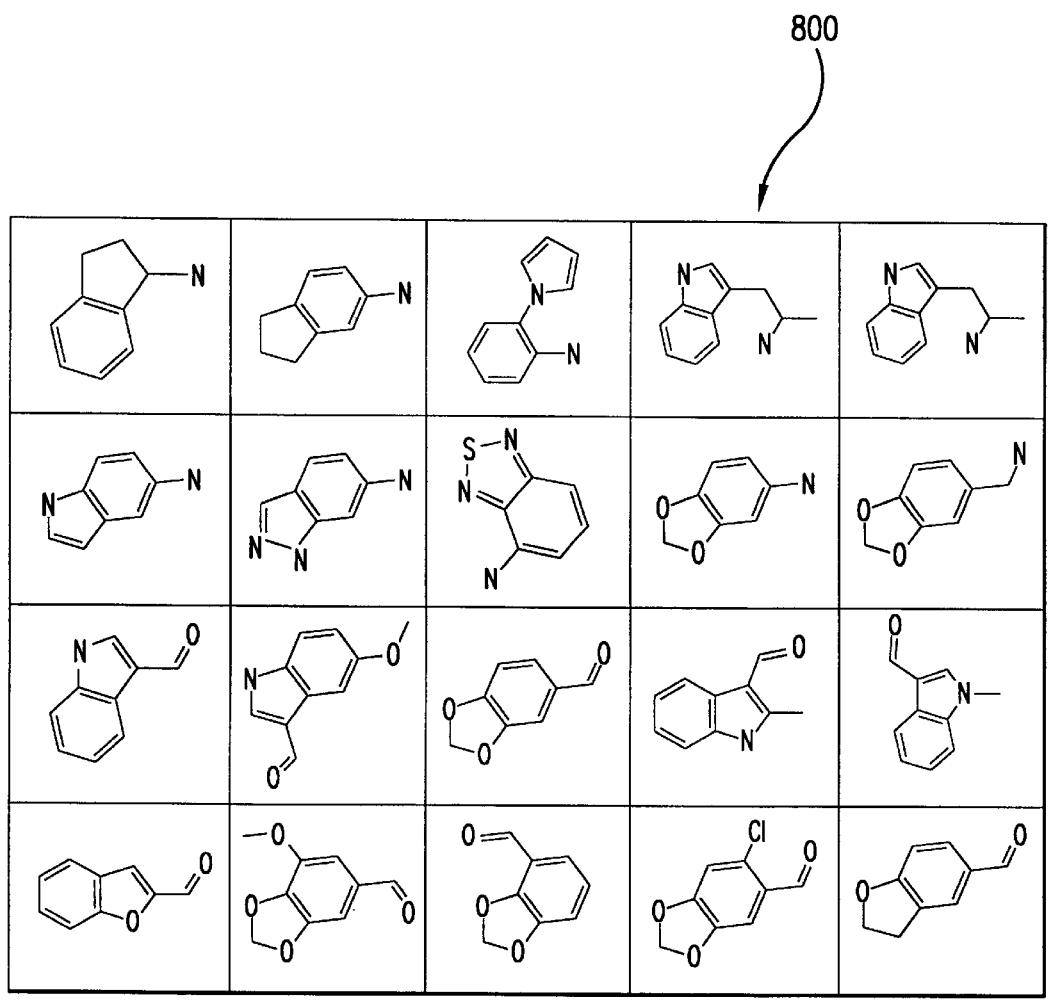
FIG. 8 is a diagram illustrating amine and aldehyde reagents that comprise a 10×10 optimum array selected from a reductive amination library according to maximum similarity to a reference structure.

FIG. 8 is a diagram 800 illustrating the amine and aldehyde reagents that comprise the 10×10 optimum array selected from the reductive amination library according to maximum similarity to reference structure 500.

To determine whether the choice and position of the lead compound has any impact on the ability of the greedy method to detect a good solution, its performance was compared relative to simulated annealing using 100 randomly chosen reference structures from the amination library. The experiment was conducted by choosing 100 compounds at random, selecting for each one the most similar 10×10 array using the methods of the present invention and simulated annealing, and comparing the scores of the resulting designs. In 13 out of 100 cases, simulated annealing produced an inferior array, while in the remaining 87 cases the two methods gave identical results.

Figure 9:
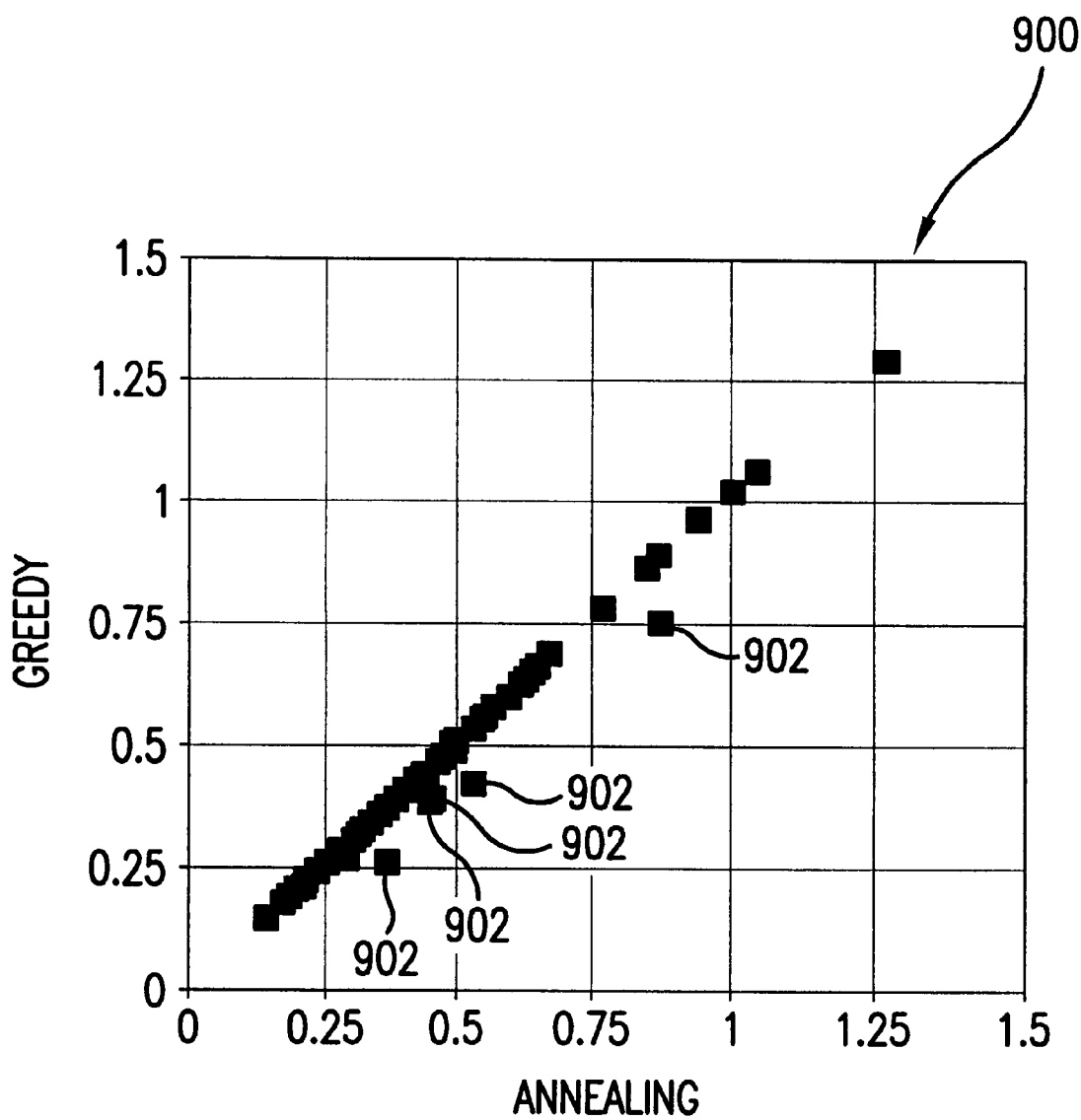
FIG. 9 is a graph showing a comparison of similarity scores of the best 10×10 arrays selected from a reductive amination library by a simulated annealing method and the greedy method of the present invention for 100 different randomly chosen leads.

FIG. 9 is a graph 900 showing a comparison of the similarity scores of the best 10×10 arrays selected from the reductive amination library by the simulated annealing method and the greedy method of the present invention for 100 different randomly chosen leads. As shown by outliers 902 in FIG. 9, in 5 of these cases, the difference between the two techniques was noticeable. Thus, although we cannot be sure that the optimum solution has been identified, it is apparent that the greedy method compares very favorably with the more elaborate and computationally demanding simulated annealing method, and appears to be capable of global optimization.

Figure 10:
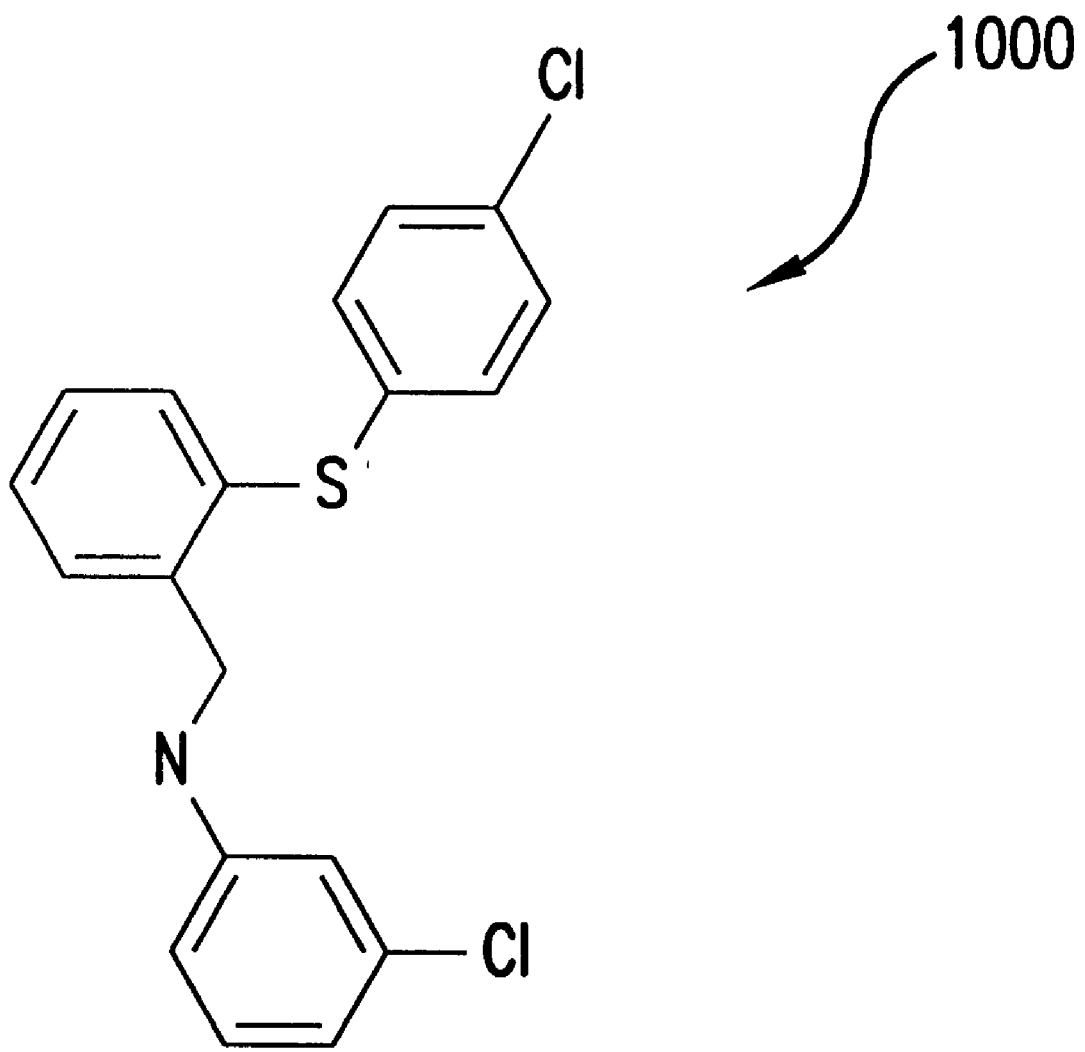
FIG. 10 is a diagram illustrating a reference structure used for similarity-based multiobjective selections from a reductive amination library.

The previous example illustrates the use of the greedy method with a function involving a single objective (similarity). In fact, this method works equally well with any objective function that can be described as a sum of individual molecular contributions. FIG. 10 is a diagram illustrating a reference structure 1000 used for similarity-based multiobjective selections from the reductive amination library. This compound has a molecular weight of 360.3 and a predicted log P of 6.46, and falls beyond the boundaries defined by the Lipinski "rule of 5," described in C. A. Lipinski et al., *Adv. Drug Delivery Rev.*, 23, 3–25 (1997), which is incorporated herein by reference in its entirety. This rule was derived from an analysis of the World Drug Index and states that for compounds which are not substrates of biological transporters, poor absorption and permeation are more likely to occur when there are more than 5 H-bond donors, more than 10 H-bond acceptors, the molecular weight is greater than 500, or the log P is greater than 5.

Figure 11A:
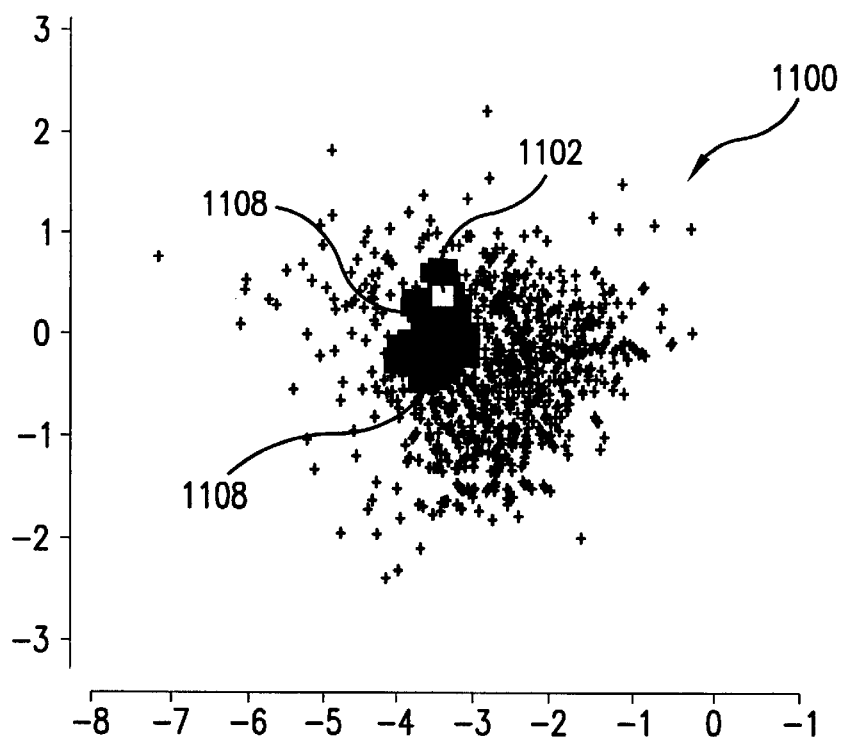
FIG. 11A is a graph illustrating the distribution of compounds in a 10×10 array selected from a reductive amination library according to maximum similarity to a reference structure for diversity space.
Figure 11B:
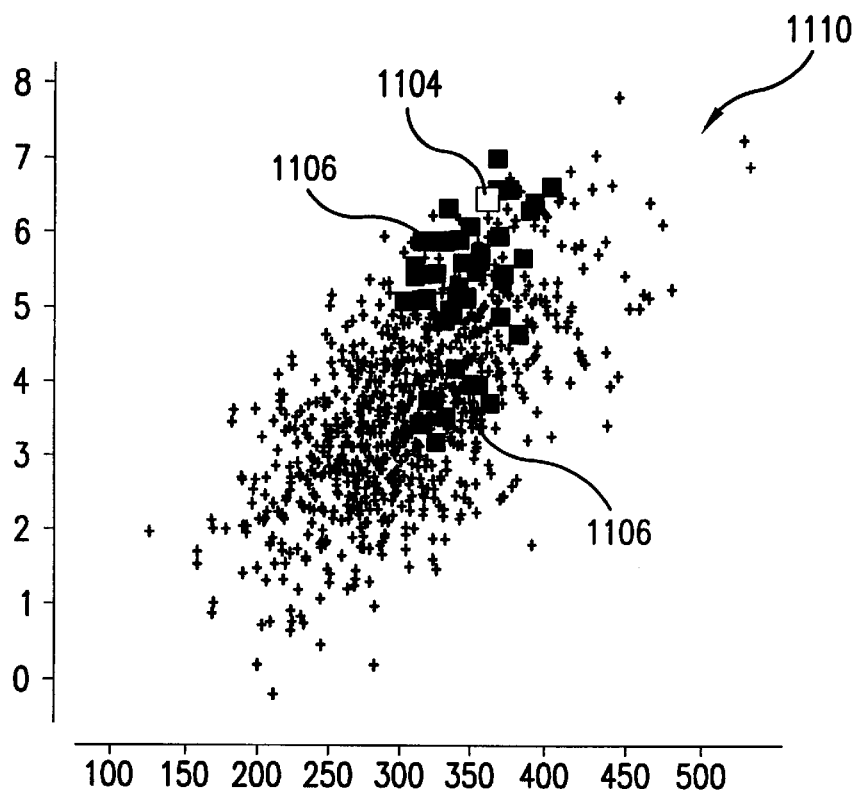
FIG. 11B is a graph illustrating the distribution of compounds in a 10×10 array selected from a reductive amination library according to maximum similarity to a reference structure for molecular weight vs computed log P.

FIG. 11A is a graph 1100 illustrating the distribution of compounds in the 10×10 array selected from the reductive amination library according to maximum similarity to reference structure 1000 in diversity space. FIG. 11B is a graph 1110 illustrating the distribution of compounds in the 10×10 array selected from the reductive amination library according to maximum similarity to reference structure 1000 in the space defined by molecular weight and computed log P. The large square (1102 and 1104 in FIGS. 11A and 11B, respectively) is the reference compound (lead), and the smaller squares (1108 and 1106 in FIGS. 11A and 11B, respectively) are the selected compounds, respectively. As shown in FIG. 11B, a 10×10 array selected based on maximum similarity to this "lead" consists of compounds with an average log P=5.47±0.85, with 77 of these compounds having a log P greater than 5.

Figure 12:
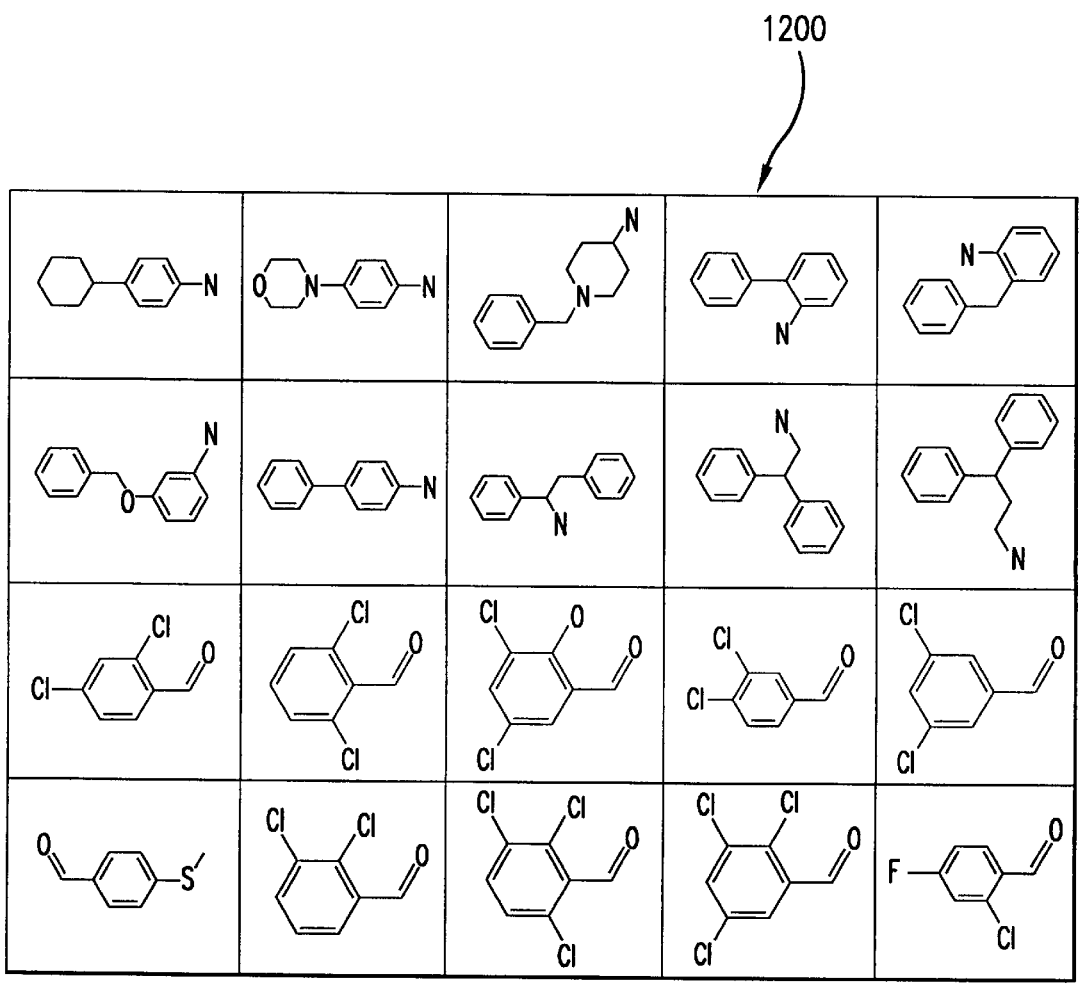
FIG. 12 is a diagram illustrating reagents comprising a 10×10 array selected from a reductive amination library according to maximum similarity to the a reference structure.

FIG. 12 is a diagram 1200 illustrating the reagents comprising the 10×10 array selected from the reductive amination library according to maximum similarity to reference structure 1000. The selected reagents consist of halogenated benzaldehydes and hydrophobic amines containing two 6-membered rings separated by a small linker. To reduce the hydrophobic character of these compounds while preserving the overall structural similarity, one can combine the molecular similarity criterion in Eq. 3 with the confinement criterion in Eq. 4 defined over the boundaries of the Lipinski box (log P≦5, MW≦500).

Figure 13A:
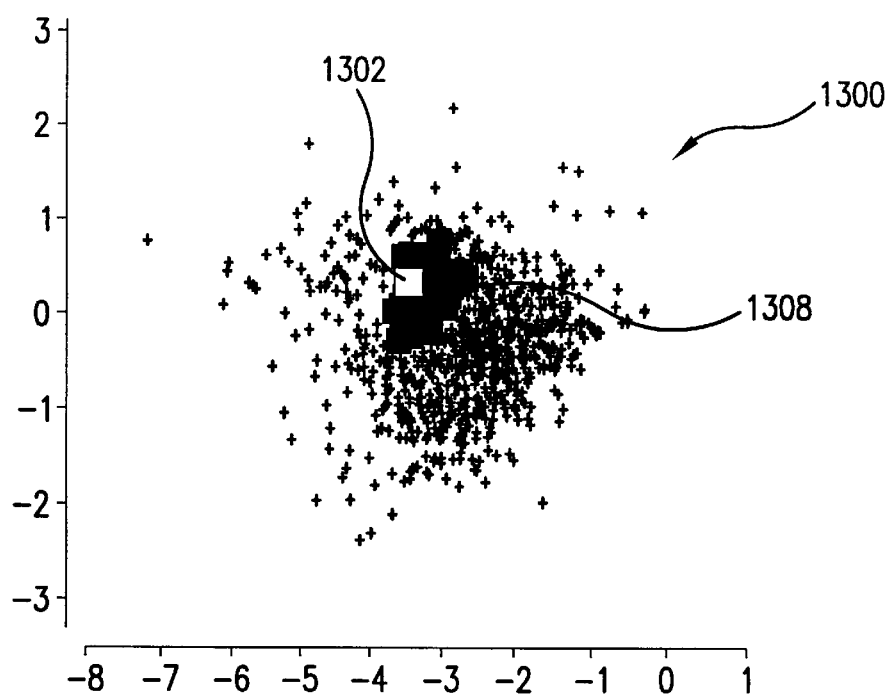
FIG. 13A is a graph 1300 illustrating a distribution of compounds in a 10×10 array selected from a reductive amination library according to a reference structure and equation (9) (shown below) for diversity space.
Figure 13B:
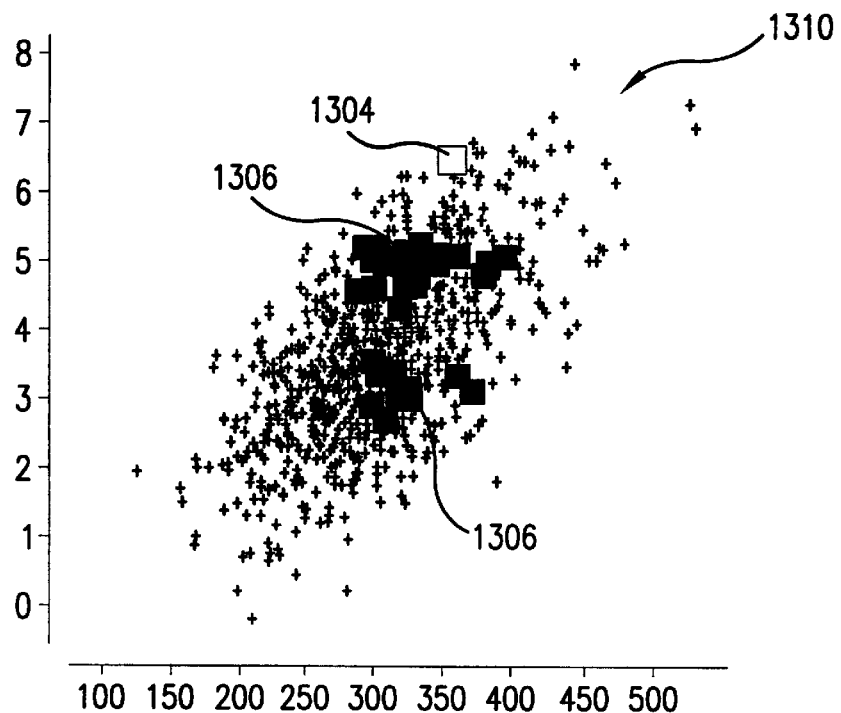
FIG. 13B is a graph illustrating a distribution of compounds in a 10×10 array selected from a reductive amination library according to a reference structure and equation (9) (shown below) for molecular weight vs computed log P.
Figure 14:
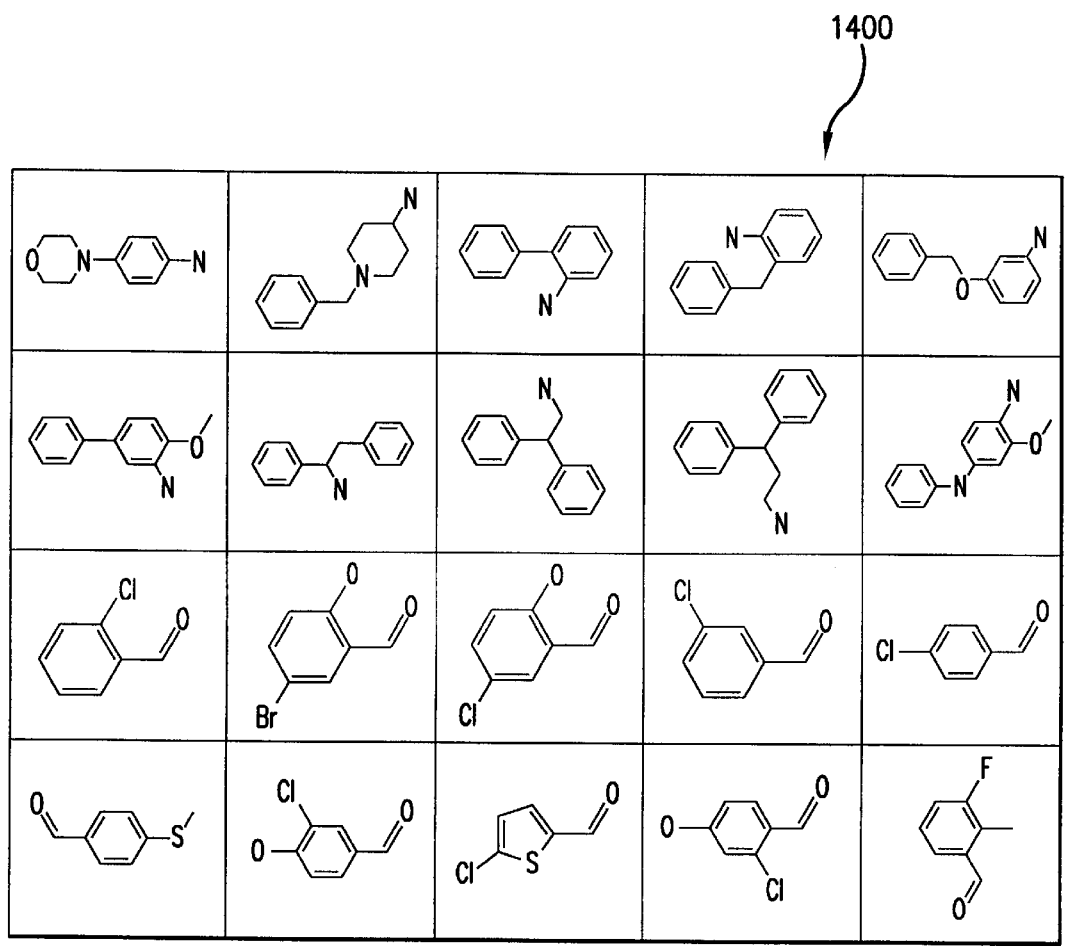
FIG. 14 is a diagram illustrating reagents comprising a 10×10 array selected from a reductive amination library according to a reference structure 1000 and equation (9) (shown below).

FIG. 13A is a graph 1300 illustrating the distribution of compounds in the 10×10 array selected from the reductive amination library according to reference structure 1000 and equation (9) (shown below) in diversity space. FIG. 13B is a graph 1310 illustrating the distribution of compounds in the 10×10 array selected from the reductive amination library according to reference structure 1000 and equation (9) (shown below) in the space defined by molecular weight and computed log P. Again, the large square (1302 and 1304 in FIGS. 13A and 13B, respectively) represents the reference compound (lead), and the smaller squares (1308 and 1306 in FIGS. 13A and 13B, respectively) represent the selected compounds, respectively. FIG. 13A and 13B show the selection of 100 compounds in 10×10 format which minimized the objective function:

$$f(C)=S(C)+2 \cdot P(C) \tag{9}$$

where S(C) and P(C) are given by Eq. 3 and Eq. 4, respectively. The weights determine the relative influence of each criterion in the final design, and were chosen based on a simple scheme described in D. N. Rassokhin et al., *J. Mol. Graphics Model*, 18(4–5), 370–384 (2000), which is incorporated herein by reference in its entirety. The resulting array consists of compounds with an average log P=4.58±0.72, and includes the reagents shown in FIG. 14. FIG. 14 is a diagram 1400 illustrating the reagents comprising the 10×10 array selected from the reductive amination library according to reference structure 1000 and equation (9). The two selections in FIGS. 12 and 14 have nine (9) reagents (eight (8) amines and one (1) aldehyde) in common. Two of the hydrophobic amines in the original selection are replaced by topologically similar structures bearing a methoxy group, while several of the polyhalogenated benzaldehydes are replaced with reagents having a smaller number of halogen substituents and, in four (4) of these cases, an additional hydroxy group. Thus, with a careful choice of parameters, the multiobjective approach is capable of guiding a selection toward more desirable regions of chemical space without destroying the primary objective of the experiment which, in this case, was the design of a series of analogues that are closely related to a known lead.

Figure 15:
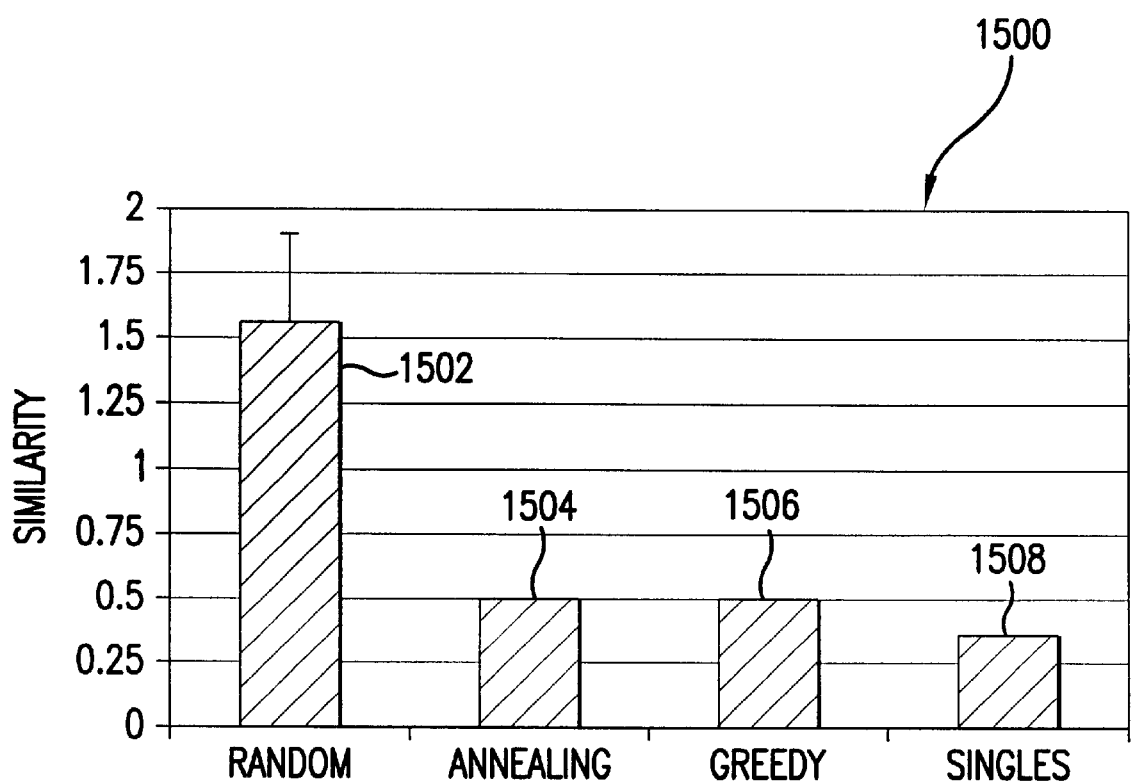
FIG. 15 is a bar chart illustrating the mean and standard deviations of similarity scores of 125 compounds selected from a diamine library according to maximum similarity to a randomly chosen structure (5×5×5 array, 125 singles), collected over 100 optimization runs.
Figure 16:
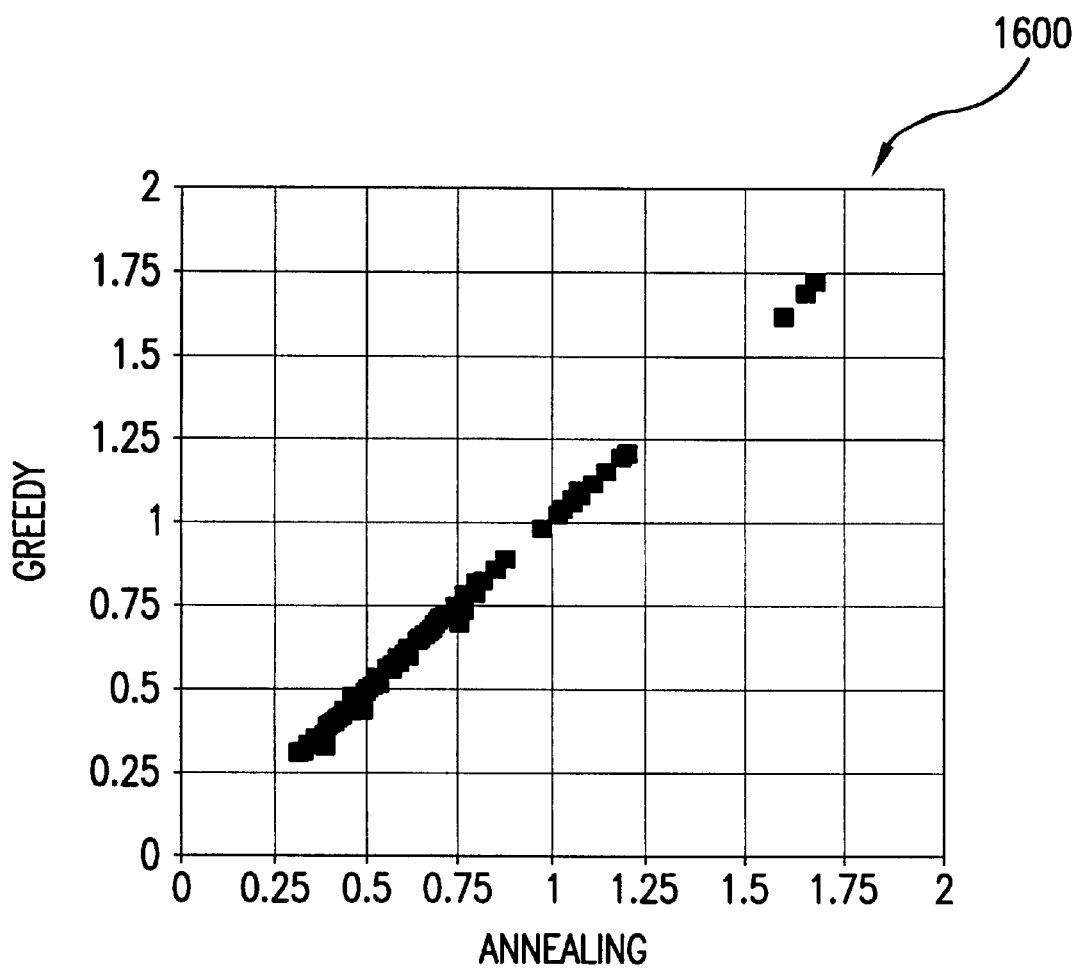
FIG. 16 is a graph 1600 illustrating a comparison of similarity scores of the best 5×5×5 arrays selected by a simulated annealing method and a greedy method of the present invention according to maximum similarity to 100 randomly chosen leads from a diamine library.

To ensure that the performance of the method of the present invention does not degrade with more complex combinatorial libraries, the same type of analysis was repeated for the 3-component diamine library described above. The results are summarized in FIGS. 15 and 16. FIG. 15 is a bar graph 1500 illustrating the mean and standard deviations of the similarity scores of 125 compounds selected from the diamine library according to maximum similarity to a randomly chosen structure (5×5×5 array, 125 singles), collected over 100 optimization runs. The results are shown for a random or chance method 1502, a simulated annealing method 1504, the greedy method 1506, and singles 1508. Once again, the greedy method was extremely robust, resulting in three distinct, but very similar solutions having an average fitness of 0.4833±0.0001; 79 out of 100 trials converged to an array with a score of 0.4832, while the remaining 21 trials converged to two different arrays with an identical score of 0.4835. Simulated annealing showed a slightly higher variability, converging to 8 different solutions with fitness values ranging from 0.4832 (the same array as that identified by the greedy method, visited 21 times) to 0.5032, and an average of 0.4859±0.0043. As with the amination library, this experiment was based on a randomly chosen "lead" from the diamine collection. The process was then repeated for 100 randomly chosen reference compounds, and the results are summarized in FIG. 16. FIG. 16 is a graph 1600 illustrating a comparison of the similarity scores of the best 5×5×5 arrays selected by the simulated annealing method and the greedy method of the present invention according to maximum similarity to 100 randomly chosen leads from the diamine library. The solutions produced by the greedy method were marginally better in 57 of these trials, marginally worse in 16 trials, and identical in the remaining 27 trials, with differences ranging from –0.059 to 0.033.

Figure 17:
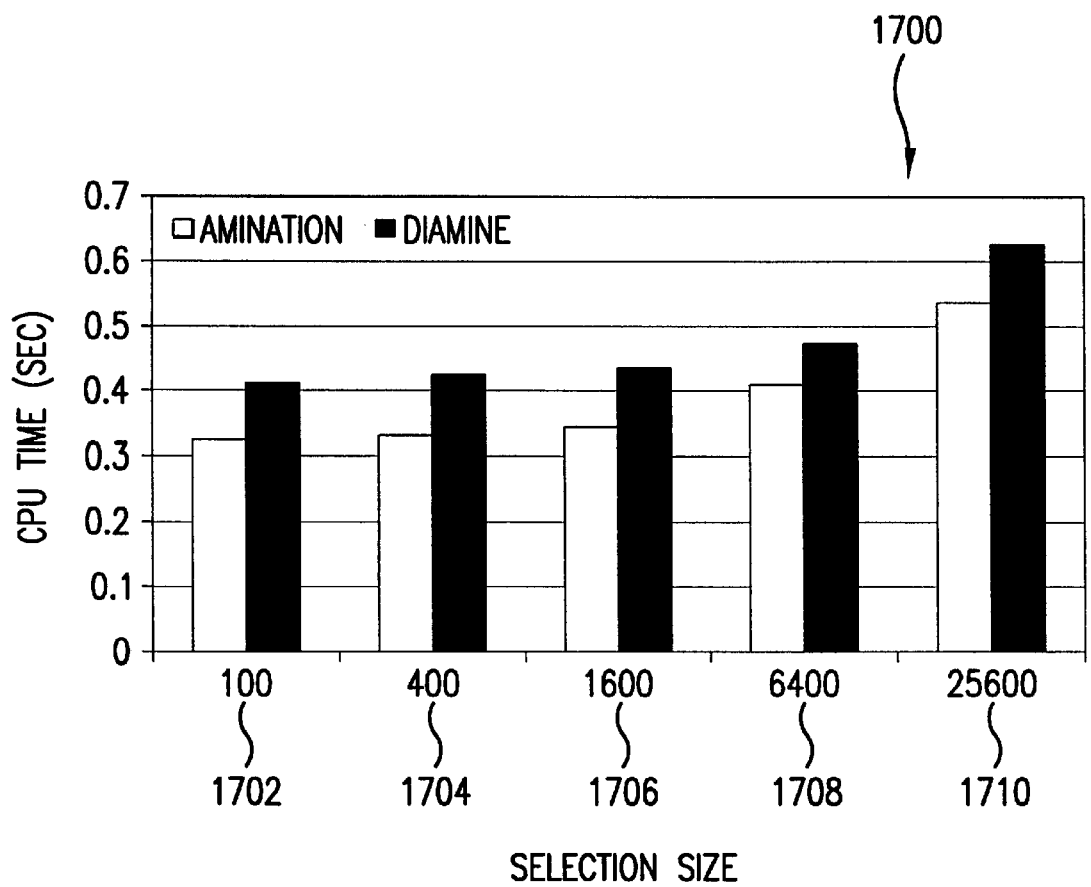
FIG. 17 is a bar graph illustrating cpu times required for the selection of 100, 400, 1600, 6400 and 25600 compounds from reductive amination and diamine libraries, respectively, using a greedy method of the present invention.

An important advantage in using the greedy method is the speed at which it executes. FIG. 17 is a bar graph illustrating the cpu times required for the selection of 100 (1702), 400 (1704), 1600 (1706), 6400 (1708) and 25600 (1710) compounds from the reductive amination and diamine libraries, respectively, using the greedy method of the present invention on a 400 MHz Intel Pentium II processor. The greedy method has trivial computational requirements and even the largest selections are completed in sub-second time frames. A significant proportion of this time is spent computing the Euclidean distances of each candidate to the respective lead during the preprocessing step, which scales linearly with the size of the virtual library. The greedy method itself scales linearly with respect to the total number of reagents, and produces solutions which are comparable to and often better than those derived from more elaborate stochastic approaches.

Implementation of the Present Invention

Figure 18:
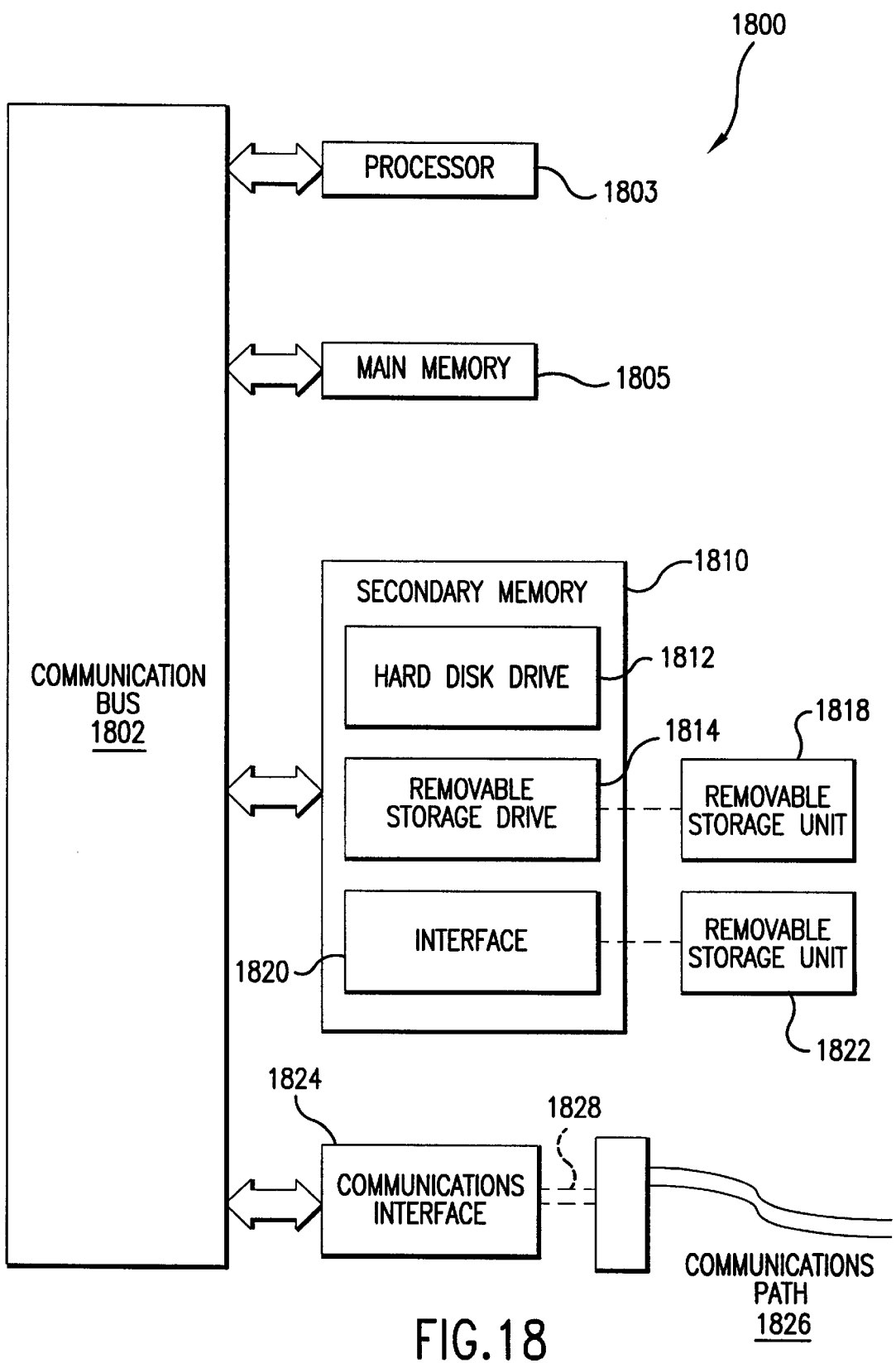
FIG. 18 is an example implementation of a computer system.

The present invention may be implemented using hardware, software, or a combination thereof and may be implemented in one or more computer systems or other processing systems. In fact, in one embodiment, the invention is directed toward one or more computer systems capable of carrying out the functionality described herein. An example implementation of a computer system 1800 is shown in FIG. 18. Various embodiments are described in terms of this exemplary computer system 1800. After reading this description, it will be apparent to a person skilled in the relevant art how to implement the invention using other computer systems and/or computer architectures. The computer system 1800 includes one or more processors, such as processor 1803. The processor 1803 is connected to a communication bus 1802.

Computer system 1800 also includes a main memory 1805, preferably random access memory (RAM), and may also include a secondary memory 1810. The secondary memory 1810 may include, for example, a hard disk drive 1812 and/or a removable storage drive 1814, representing a floppy disk drive, a magnetic tape drive, an optical disk drive, etc. The removable storage drive 1814 reads from and/or writes to a removable storage unit 1818 in a well-known manner. Removable storage unit 1818, represents a floppy disk, magnetic tape, optical disk, etc., which is read by and written to by removable storage drive 1814. As will be appreciated, the removable storage unit 1818 includes a computer usable storage medium having stored therein computer software and/or data.

In alternative embodiments, secondary memory 1810 may include other similar means for allowing computer programs or other instructions to be loaded into computer system 1800. Such means may include, for example, a removable storage unit 1822 and an interface 1820. Examples of such may include a program cartridge and cartridge interface (such as that found in video game devices), a removable memory chip (such as an EPROM, or PROM) and associated socket, and other removable storage units 1822 and interfaces 1820 which allow software and data to be transferred from the removable storage unit 1822 to computer system 1800.

Computer system 1800 may also include a communications interface 1824. Communications interface 1824 allows software and data to be transferred between computer system 1800 and external devices. Examples of communications interface 1824 may include a modem, a network interface (such as an Ethernet card), a communications port, a PCMCIA slot and card, a wireless LAN (local area network) interface, etc. Software and data transferred via communications interface 1824 are in the form of signals 1828 which may be electronic, electromagnetic, optical, or other signals capable of being received by communications interface 1824. These signals 1828 are provided to communications interface 1824 via a communications path (i.e., channel) 1826. This channel 1826 carries signals 1828 and may be implemented using wire or cable, fiber optics, a phone line, a cellular phone link, a wireless link, and other communications channels.

In this document, the term []computer program product refers to removable storage units 1818, 1822, and signals 1828. These computer program products are means for providing software to computer system 1800.

The invention is directed to such computer program products.

Computer programs (also called computer control logic) are stored in main memory 1805, and/or secondary memory 1810 and/or in computer program products. Computer programs may also be received via communications interface 1824. Such computer programs, when executed, enable the computer system 1800 to perform the features of the present invention as discussed herein. In particular, the computer programs, when executed, enable the processor 1803 to perform the features of the present invention. Accordingly, such computer programs represent controllers of the computer system 1800.

In an embodiment where the invention is implemented using software, the software may be stored in a computer program product and loaded into computer system 1800 using removable storage drive 1814, hard drive 1812 or communications interface 1824. The control logic (software), when executed by the processor 1803, causes the processor 1803 to perform the functions of the invention as described herein.

In another embodiment, the invention is implemented primarily in hardware using, for example, hardware components such as application specific integrated circuits (ASICs). Implementation of hardware state machine(s) so as to perform the functions described herein will be apparent to persons skilled in the relevant art(s).

In yet another embodiment, the invention is implemented using a combination of both hardware and software.

Conclusion

While various embodiments of the present invention have been described above, it should be understood that they have been presented by way of example only, and not limitation. It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A method for designing combinatorial arrays, comprising the steps of:
   (1) determining a number of reagents to be selected from a plurality of variation sites in a combinatorial library, wherein said number of reagents is smaller than or equal to a number of candidate reagents at each of said variation sites in said combinatorial library;
   (2) selecting said number of reagents from a plurality of candidate reagents at each of said variation sites in said combinatorial library;
   (3) evaluating fitness (f') of a combinatorial array resulting from the systematic combination of said number of reagents selected in step (2);
   (4) independently evaluating a plurality of candidate reagents from one of said variation sites in said combinatorial library by evaluating combinatorial sub-arrays resulting from the systematic combination of each of said plurality of candidate reagents from said one of said variation sites in said combinatorial library with the selected reagents from each of said variation sites other than said one of said variation sites in said combinatorial library;
   (5) ranking each of said candidate reagents in said plurality of candidate reagents from said one of said variation sites in said combinatorial library based on results obtained in step (4);
   (6) selecting a new set of reagents from said plurality of candidate reagents from said one of said variation sites in said combinatorial library based on the results of said ranking step;
   (7) repeating steps (4), (5) and (6) for each of said variation sites in said combinatorial library;
   (8) evaluating fitness (f) for a combinatorial array resulting from the systematic combination of the selected reagents at each of said variation sites in said combinatorial library;
   (9) setting f' equal to f and repeating steps (4) through (8), if f is a better fitness than f'; and
   (10) outputting said combinatorial array from step (8), if f is not a better fitness than f'.

2. The method of claim 1, wherein steps (3), (4), and (8) are evaluated based on one or more objective functions.

3. The method of claim 1, wherein steps (3), (4), and (8) are evaluated based on the similarity of compounds comprising said combinatorial array and/or said combinatorial sub-array(s) to at least one given reference compound.

4. The method of claim 1, wherein steps (3), (4), and (8) are evaluated based on the degree of matching of compounds comprising said combinatorial array and/or said combinatorial sub-array(s) against at least one query or probe.

5. The method of claim 1, wherein steps (3), (4), and (8) are evaluated based on at least one property of compounds comprising said combinatorial array and/or said combinatorial sub-array(s).

6. The method of claim 5, wherein said at least one property of compounds comprising said combinatorial array and/or said combinatorial sub-array(s) is a computed property.

7. The method of claim 1, wherein step (2) comprises the step of selecting said number of reagents from said plurality of candidate reagents at each of said variation sites in said combinatorial library at random.

8. The method of claim 1, wherein step (2) comprises the step of selecting said number of reagents from said plurality of candidate reagents at each of said variation sites in said combinatorial library systematically or semi-systematically.

9. The method of claim 1, wherein steps (2)–(10) are repeated at least two times.

10. The method of claim 1, wherein step (2) comprises the step of selecting said number of reagents from said plurality of candidate reagents at each of said variation sites in said combinatorial library so that the selected reagents from at least one of said variation sites contain at least one given reagent.

11. The method of claim 1, wherein step (6) comprises the step of selecting said new set of reagents from said plurality of candidate reagents at each of said variation sites in said combinatorial library based on rankings determined in step (5) so that said new set of selected reagents at said one of said variation sites in said combinatorial library contains at least one given reagent.

12. A computer program product comprising a computer useable medium having computer program logic recorded thereon for enabling a computer to design combinatorial arrays, said computer program logic comprising:

determining means for enabling a processor to determine a number of reagents to be selected from a plurality of variation sites in a combinatorial library, wherein said number of reagents is smaller than or equal to a number of candidate reagents at each of said variation sites in said combinatorial library;

selecting means for enabling a processor to select said number of reagents from a plurality of candidate reagents at each of said variation sites in said combinatorial library;

first evaluating means for enabling a processor to evaluate fitness (f') of a combinatorial array resulting from the systematic combination of said number of reagents resulting from said selecting means;

independently evaluating means for enabling a processor to independently evaluate a plurality of candidate reagents from one of said variation sites in said combinatorial library by evaluating combinatorial sub-arrays resulting from the systematic combination of each of said plurality of candidate reagents from said one of said variation sites in said combinatorial library with the selected reagents from each of said variation sites other than said one of said variation sites in said combinatorial library;

ranking means for enabling a processor to rank each of said candidate reagents in said plurality of candidate reagents from said one of said variation sites in said combinatorial library based on results obtained in said independently evaluating means;

selecting means for enabling a processor to select a new set of reagents from said plurality of candidate reagents from said one of said variation sites in said combinatorial library based on the results of said ranking means;

ranking and selecting means for enabling a processor to rank and select reagents at each of said variation sites in said combinatorial library in turn;

second evaluating means for enabling a processor to evaluate fitness (f) for the combinatorial array resulting from the systematic combination of the selected reagents at each of said variation sites in said combinatorial library;

means for enabling a processor to determine if f is a better fitness than f';

means for enabling a processor to redesign said combinatorial array until f is not a better fitness than f';

setting means for enabling a processor to set f' equal to f, if f is a better fitness than f'; and outputting means for enabling a processor to output said combinatorial array.

13. The computer program product of claim 12, wherein said first evaluating means, said independently evaluating means, and said second evaluating means are evaluated based on one or more objective functions.

14. The computer program product of claim 12, wherein said first evaluating means, said independently evaluating means, and said second evaluating means are evaluated based on the similarity of compounds comprising said combinatorial array and/or said combinatorial sub-array(s) to at least one given reference compound.

15. The computer program product of claim 12, wherein said first evaluating means, said independently evaluating means, and said second evaluating means are evaluated based on the degree of matching of compounds comprising said combinatorial array and/or said combinatorial sub-array (s) against at least one query or probe.

16. The computer program product of claim 12, wherein said first evaluating means, said independently evaluating means, and said second evaluating means are evaluated based on at least one property of compounds comprising said combinatorial array and/or said combinatorial sub-array (s).

17. The computer program product of claim 16, wherein said at least one property of compounds comprising said combinatorial array and/or said combinatorial sub-array(s) is a computed property.

18. The computer program product of claim 12, wherein said selecting means for enabling a processor to select said number of reagents from a plurality of candidate reagents at each of said variation sites in said combinatorial library further comprises means for enabling a processor to select said number of reagents from said plurality of candidate reagents at each of said variation sites in said combinatorial library at random.

19. The computer program product of claim 12, wherein said selecting means for enabling a processor to select said number of reagents from a plurality of candidate reagents at each of said variation sites in said combinatorial library further comprises means for enabling a processor to select said number of reagents from said plurality of candidate reagents at each of said variation sites in said combinatorial library systematically or semi-systematically.

20. The computer program product of claim 12, wherein said selecting means for enabling a processor to select said number of reagents from a plurality of candidate reagents at each of said variation sites in said combinatorial library further comprises means for enabling a processor to select said number of reagents from said plurality of candidate reagents at each of said variation sites in said combinatorial library so that the selected reagents from at least one of said variation sites contain at least one given reagent.

21. The computer program product of claim 12, wherein said selecting means for enabling a processor to select a new set of reagents from said plurality of candidate reagents from said one of said variation sites in said combinatorial library based on the results of said ranking means further comprises means for enabling a processor to select said new set of reagents from said plurality of candidate reagents at each of said variation sites in said combinatorial library based on said ranking means so that said new set of selected reagents at said one of said variation sites in said combinatorial library contains at least one given reagent.

* * * * *